(12) United States Patent
Busby

(10) Patent No.: US 12,097,370 B2
(45) Date of Patent: Sep. 24, 2024

(54) MULTIMODAL PRESCRIPTION TECHNIQUES

(71) Applicant: Cochlear Limited, Macquarie University (AU)

(72) Inventor: Peter Andrew Busby, Caulfield (AU)

(73) Assignee: Cochlear Limited, Macquarie University (AU)

( * ) Notice: Subject to any disclaimer, the term of this patent is extended or adjusted under 35 U.S.C. 154(b) by 1036 days.

(21) Appl. No.: 16/245,677

(22) Filed: Jan. 11, 2019

(65) Prior Publication Data

US 2019/0143115 A1 May 16, 2019

Related U.S. Application Data

(63) Continuation of application No. 15/238,139, filed on Aug. 16, 2016, now Pat. No. 10,179,240.

(51) Int. Cl.
*A61N 1/36* (2006.01)
*A61B 5/00* (2006.01)
*A61B 5/12* (2006.01)
*A61N 1/372* (2006.01)
*H04R 25/00* (2006.01)

(52) U.S. Cl.
CPC .......... *A61N 1/36036* (2017.08); *A61B 5/125* (2013.01); *A61B 5/4851* (2013.01); *A61N 1/36038* (2017.08); *A61N 1/37247* (2013.01); *H04R 25/353* (2013.01); *H04R 25/70* (2013.01); *H04R 25/606* (2013.01); *H04R 2225/67* (2013.01); *H04R 2460/13* (2013.01)

(58) Field of Classification Search
CPC .............................. A61N 1/05; A61N 1/36036
USPC ....................... 607/55, 57, 123; 600/379, 559
See application file for complete search history.

(56) References Cited

U.S. PATENT DOCUMENTS

| | | | | |
|---|---|---|---|---|
| 8,086,319 | B2 * | 12/2011 | van Dijk | A61N 1/36036 600/379 |
| 2006/0287690 | A1 * | 12/2006 | Bouchataoui | A61N 1/36039 607/57 |
| 2007/0135862 | A1 * | 6/2007 | Nicolai | A61N 1/36039 607/56 |
| 2014/0270210 | A1 * | 9/2014 | van Dijk | H04R 25/70 381/60 |
| 2016/0080878 | A1 * | 3/2016 | Hillbratt | H04R 25/558 381/315 |
| 2017/0064462 | A1 * | 3/2017 | Warren | H04R 25/353 |

* cited by examiner

*Primary Examiner* — Jon Eric C Morales
(74) *Attorney, Agent, or Firm* — Pilloff Passino & Cosenza LLP; Martin J. Cosenza

(57) ABSTRACT

A method, including obtaining data relating to electric hearing, obtaining data relating to acoustic hearing and preparing a prescription for a multimodal hearing prosthesis for an individual based on the obtained data relating to the electric hearing and the acoustic hearing. In an exemplary embodiment, the method entails comparing the data relating to electric hearing to the data relating to acoustic hearing and preparing the prescription based on the results of the comparison.

34 Claims, 23 Drawing Sheets

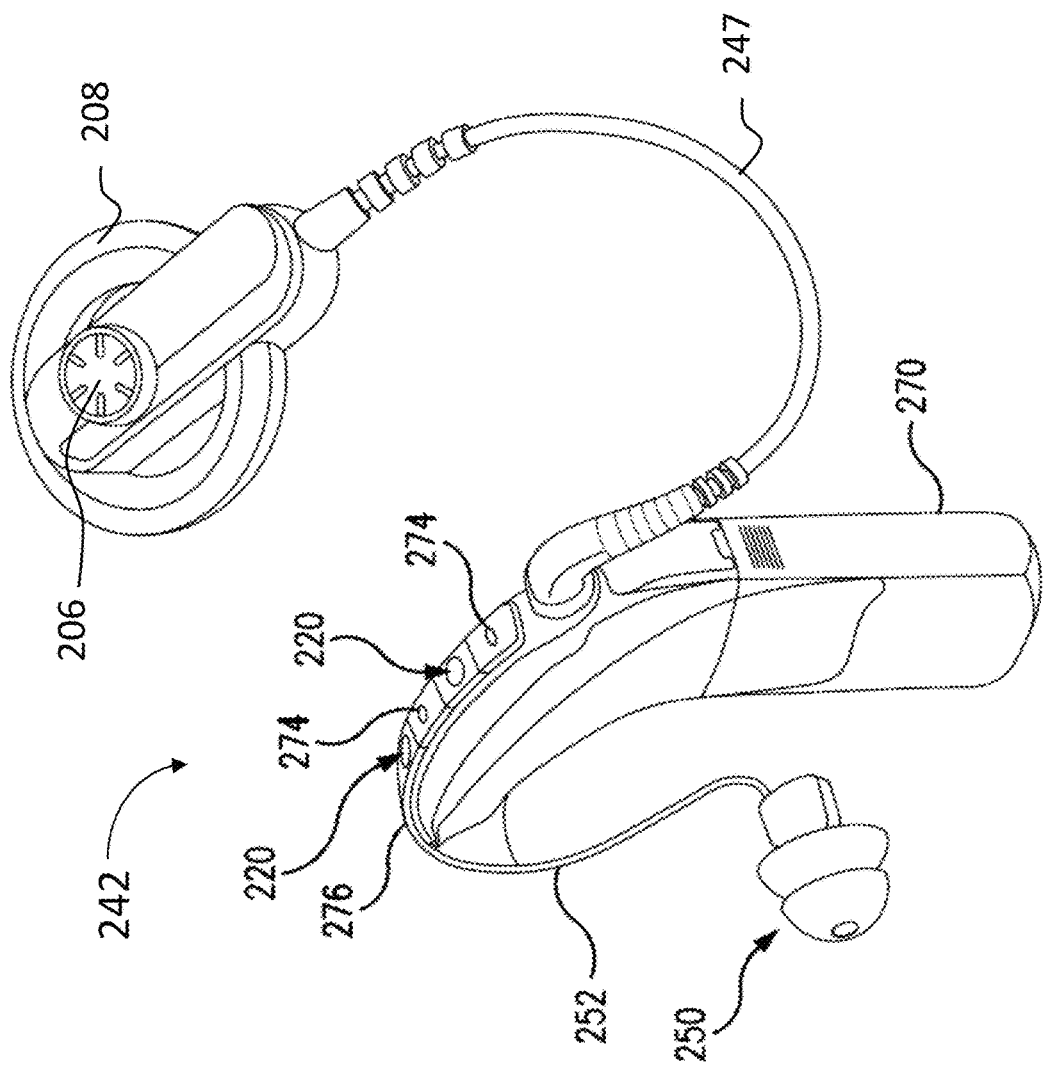

MULTIMODAL PRESCRIPTION TECHNIQUES

CROSS-REFERENCE TO RELATED APPLICATIONS

This application is a Continuation application of U.S. patent application Ser. No. 15/238,139, filed Aug. 16, 2016, entitled MULTIMODAL PRESCRIPTION TECHNIQUES, naming Peter Andrew BUSBY of Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is a method, comprising obtaining data relating to electric hearing, obtaining data relating to acoustic hearing, and preparing a prescription for a hearing prosthesis for an individual based on the obtained data relating to the electric hearing and the acoustic hearing.

In accordance with another exemplary embodiment, there is a method comprising setting a cochlear implant to operate based on data based on a comparison of first data for electric stimulation to evoke a hearing percept with second data for a second type of stimulation to evoke a hearing percept different from the electric stimulation.

In accordance with another exemplary embodiment, there is a method comprising obtaining normative data indicative of respective contributions to speech understanding for respective frequency bands of cochlear implants, obtaining data indicative of respective contributions to speech understanding for the respective frequency bands for non-cochlear implant hearing, and analyzing the obtained data and setting a multimodal prosthesis including a cochlear implant to operate based on the comparison.

BRIEF DESCRIPTION OF THE DRAWINGS

Embodiments are described below with reference to the attached drawings, in which:

FIG. 1B is another view of the exemplary multimodal hearing prosthesis presented in FIG. 1A;

DETAILED DESCRIPTION

Figure 1A:
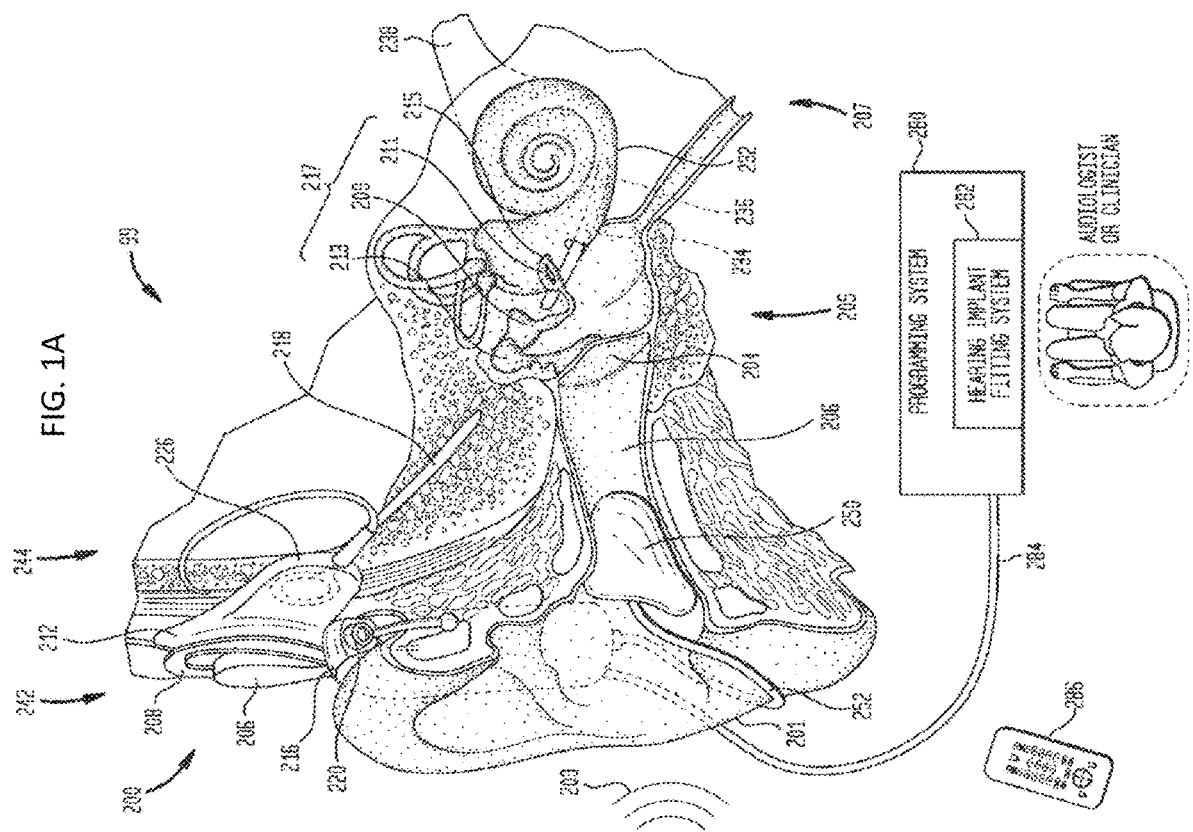
FIG. 1A is a perspective view of an exemplary multimodal hearing prosthesis according to an exemplary embodiment.

FIG. 1A is a perspective view of an exemplary multimodal prosthesis in which the present invention may be implemented. The ear 99 includes outer ear 201, middle ear 205, and inner ear 207 are described next below, followed by a description of an implanted multimodal system 200. Multimodal system 200 provides multiple types of stimulation, i.e., acoustic, electrical, and/or mechanical. These different stimulation modes may be applied ipsilaterally or contralaterally. In the embodiment shown in FIG. 1A, multimodal implant 200 provides acoustic and electrical stimulation, although other combinations of modes can be implemented in some embodiments. By way of example and not by way of limitation, a middle-ear implant can be utilized in combination with the cochlear implant, a bone conduction device can be utilized in combination with the cochlear implant, etc.

In a person with normal hearing or a recipient with residual hearing, an acoustic pressure or sound wave 203 is collected by outer ear 201 (that is, the auricle) and channeled into and through ear canal 206. Disposed across the distal end of ear canal 206 is a tympanic membrane 204 which vibrates in response to acoustic wave 203. This vibration is coupled to oval window, fenestra ovalis 215 through three bones of middle ear 205, collectively referred to as the ossicles 217 and comprising the malleus 213, the incus 209, and the stapes 211. Bones 213, 209, and 211 of middle ear 205 serve to filter and transfer acoustic wave 203, causing oval window 215 to articulate, or vibrate. Such vibration sets up waves of fluid motion within cochlea 232. Such fluid motion, in turn, activates tiny hair cells (not shown) that line the inside of cochlea 232. Activation of the hair cells causes appropriate nerve impulses to be transferred through the spiral ganglion cells (not shown) and auditory nerve 238 to the brain (not shown), where such pulses are perceived as sound.

In individuals with a hearing deficiency who may have some residual hearing, an implant or hearing instrument may improve that individual's ability to perceive sound. Multimodal prosthesis 200 may comprises external component assembly 242 which is directly or indirectly attached to the body of the recipient, and an internal component assembly 244 which is temporarily or permanently implanted in the recipient. External component assembly is also shown in FIG. 1B. In embodiments of the present invention, components in the external assembly 242 may be included as part of the implanted assembly 244, and vice versa. Also, embodiments of the present invention may be used with implanted multimodal system 200 which are fully implanted.

External assembly 242 typically comprises a sound transducer 220 for detecting sound, and for generating an electrical audio signal, typically an analog audio signal. In this illustrative embodiment, sound transducer 220 is a microphone. In alternative embodiments, sound transducer 220 can be any device now or later developed that can detect sound and generate electrical signals representative of such sound.

Figure 1C:
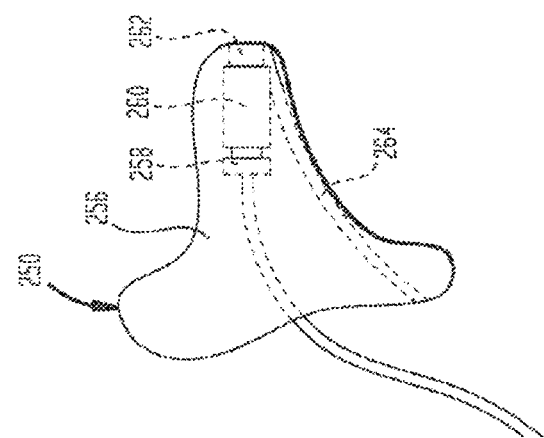
FIG. 1C provides additional details of the exemplary multimodal hearing prosthesis of FIG. 1B.

External assembly 242 also comprises a signal processing unit, a power source (not shown), and an external transmitter unit. External transmitter unit 206 comprises an external coil 208 and, preferably, a magnet (not shown) secured directly or indirectly to the external coil 208. Signal processing unit processes the output of microphone 220 that is positioned, in the depicted embodiment, by outer ear 201 of the recipient. Signal processing unit generates coded signals, referred to herein as a stimulation data signals, which are provided to external transmitter unit 206 via a cable 247 and to the receiver in the ear 250 via cable 252. FIG. 1C provides additional details of an exemplary receiver 250. The overall component containing the signal processing unit is, in this illustration, constructed and arranged so that it can fit behind outer ear 201 in a BTE (behind-the-ear) configuration, but may also be worn on different parts of the recipient's body or clothing.

In some embodiments, signal processor may produce electrical stimulations alone, without generation of any acoustic stimulation beyond those that naturally enter the ear. While in still further embodiments, two signal processors may be used. One signal processor is used for generating electrical stimulations in conjunction with a second speech processor used for producing acoustic stimulations.

As shown in FIGS. 1B and 1C, a receiver in the ear 250 is connected to signal processor through cable 252. Receiver in the ear 250 includes a housing 256, which may be a molding shaped to the recipient. Inside receiver in the ear 250 there is provided a capacitor 258, receiver 260 and protector 262. Also, there may a vent shaft 264 (in some embodiments, this vent shaft is not included). Receiver in the ear may be an in-the-ear (ITE) or completely-in-canal (CIC) configuration.

Also, FIG. 1B shows a removable battery 270 directly attached to the body/spine of the BTE device. As seen, the BTE device in some embodiments control buttons 274. In addition, the BTE may house a power source (not shown), e.g., zinc-air batteries. The BTE device may have an indicator light 276 on the earhook to indicate operational status of signal processor. Examples of status indications include a flicker when receiving incoming sounds, low rate flashing when power source is low or high rate flashing for other problems.

Returning to FIG. 1A, internal components 244 comprise an internal receiver unit 212, a stimulator unit 226 and an electrode assembly 218. Internal receiver unit 212 comprises an internal transcutaneous transfer coil (not shown), and preferably, a magnet (also not shown) fixed relative to the internal coil. Internal receiver unit 212 and stimulator unit 226 are hermetically sealed within a biocompatible housing. The internal coil receives power and data from external coil 208, as noted above. A cable or lead of electrode assembly 218 extends from stimulator unit 226 to cochlea 232 and terminates in an array 234 of electrodes 236. Electrical signals generated by stimulator unit 226 are applied by electrodes 236 to cochlea 232, thereby stimulating the auditory nerve 238.

In one embodiment, external coil 208 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 212 may be positioned in a recess of the temporal bone adjacent to outer ear 201 of the recipient.

As shown in FIG. 1A, multimodal system 200 is further configured to interoperate with a user interface 280 and an external processor 282 such as a personal computer, workstation, or the like, implementing, for example, a hearing implant fitting system. Although a cable 284 is shown in FIG. 1A between implant 200 and interface 280, a wireless RF communication may also be used along with remote 286.

While FIG. 1A shows a multimodal implant in the ipsilateral ear, in other embodiments of the present invention the multimodal implant may provide stimulation to both ears. For example, a signal processor may provide electrical stimulation to one ear and provide acoustical stimulation in the other ear.

Using an exemplary multimodal device shown in FIGS. 1A and 1B, the prescription process that embodiments of the present invention may use is described in the following systems and methods.

In at least some exemplary embodiments, there is utilitarian value with respect to determining what frequency bands the multimodal prosthesis 200 will allocate towards electric hearing (e.g., hearing based on the utilization of the electrode assembly 218) and acoustic hearing (e.g., hearing that is prompted by the in the ear device 250 in general, and the projector 262 in particular and/or hearing that will be left to natural means (e.g., no amplification)). It is noted that by allocating frequency bands to acoustic hearing, this can include leaving those frequency bands to natural hearing. That is, the multimodal prosthesis 200 can be such that frequency bands allocated to acoustic hearing simply result in no action by the prosthesis 200 at all. That said, in at least some exemplary embodiments, such as those that utilize the ITE device 250, those frequency bands for acoustic hearing will be provided to the ITE device 250 so that the projector 262 can output and acoustic signal in an amplified manner to evoke a hearing percept akin to that which corresponds to the utilization of a conventional hearing aid, at least for those channels/frequencies.

The utilitarian value associated with determining what frequency bands the multimodal prosthesis 200 will allocate towards electric hearing and acoustic hearing can result in the maximizing of acoustic hearing, but only for frequency bands where such is utilitarian to do so. In an exemplary embodiment, the teachings detailed herein are directed towards identifying the frequency bands where acoustic hearing provides more utilitarian value to the recipient than that which would be the case if those frequency bands were instead allocated towards electric hearing (e.g., the electrode assembly 218 was activated so as to evoke a hearing percept corresponding to those frequency bands/based on those frequency bands) and/or identifying the frequency bands where electric hearing provides more utilitarian value to the recipient than that which would be the case if those frequency bands were instead allocated towards acoustic hearing (e.g., the electrode assembly 218 was not activated, thus preventing an electrical-based hearing percept corresponding to those frequency bands/based on those frequency bands). Hereinafter, the bifurcation between acoustic hearing and electric hearing is sometimes referred to as the acoustic-to-electric cross-over frequency.

In general terms, in a given exemplary scenario of use, for a newly implanted cochlear implant recipient with residual hearing in the implanted ear (or another ear—more on this below), there can be utilitarian value with respect to determining the acoustic-to-electric cross-over frequency. Again, it is noted that while the teachings detailed herein are described in terms of the multimodal prosthesis 200, that includes the ITE 250 with the projector 262, in some alternate embodiments, the teachings detailed herein are applicable to a unimodal prosthesis corresponding to a cochlear implant without an acoustic hearing aid (receiver 250 having the projector 262).

In some exemplary embodiments where the recipient has residual hearing, the prosthesis, whether such is a multimodal prosthesis 200 or unimodal prosthesis in the form of a cochlear implant, the prosthesis is "fitted" to the recipient. The details of such fitting entail activating the prosthesis in general, and the electrode array/electrode assembly 218 of the cochlear implant in particular, while implanted in the recipient, to evoke a hearing percept, and adjust settings of the prosthesis based on the particular recipient's physiology/reactions to the stimulus from the prosthesis. In at least some exemplary embodiments, this entails setting so-called threshold and comfort levels. In at least some exemplary embodiments, this entails tonotopically mapping the various channels of the cochlear implant. The teachings detailed herein are applicable to pre-fitting actions associated with the prosthesis. Indeed, in an exemplary embodiment, the teachings are directed towards developing a prescription for a given recipient and/or for a class of recipients prior to implantation of the cochlear implant and/or prior to the first activation of the cochlear implant to evoke a hearing percept, or at least prior to the first fitting session of the cochlear implant to the recipient.

Some exemplary embodiments are directed towards developing a prescription that maximizes acoustic hearing in general, and maximizes speech understanding resulting from acoustic hearing in particular, but only where such has utilitarian value vis-à-vis obtaining superior results. Again, if electric hearing provides a more utilitarian result with respect to a given frequency band, such as providing more utilitarian speech understanding than that which would be the case with respect to the acoustic hearing, the maximization of acoustic hearing at this frequency band would not have utilitarian value with respect to obtaining greater speech understanding relative to that which would be the case if this frequency band was allocated to the electric hearing. With respect to the aforementioned fitting process, it is not known at the time of the first fitting what the maximum benefit that can be achieved from allocating a frequency band to electric hearing, compared to allocating that band to acoustic hearing. In at least some exemplary embodiments, this is because the recipient has no experience with electrical hearing.

Indeed, in an exemplary embodiment, the teachings detailed herein and/or variations thereof can be considered pre-fitting methods. In some exemplary embodiments, the teachings detailed herein and/or variations thereof are provided so as to establish a baseline from which an audiologist works during the fitting process. That is, in an exemplary embodiment, the teachings detailed herein can provide an audiologist with the initial settings of the cochlear implant vis-à-vis which frequency bands to allocate to electric hearing and which frequency bands to allocate to non-electric hearing, and the audiologist then works from there to fine-tune the prostheses based on traditional fitting methods. In some exemplary embodiments, the teachings detailed herein and/or variations thereof can have utilitarian value with respect to providing a probability or likelihood estimate that a given band will provide more or less information than the acoustic hearing when allocated to electric hearing.

Figure 2:
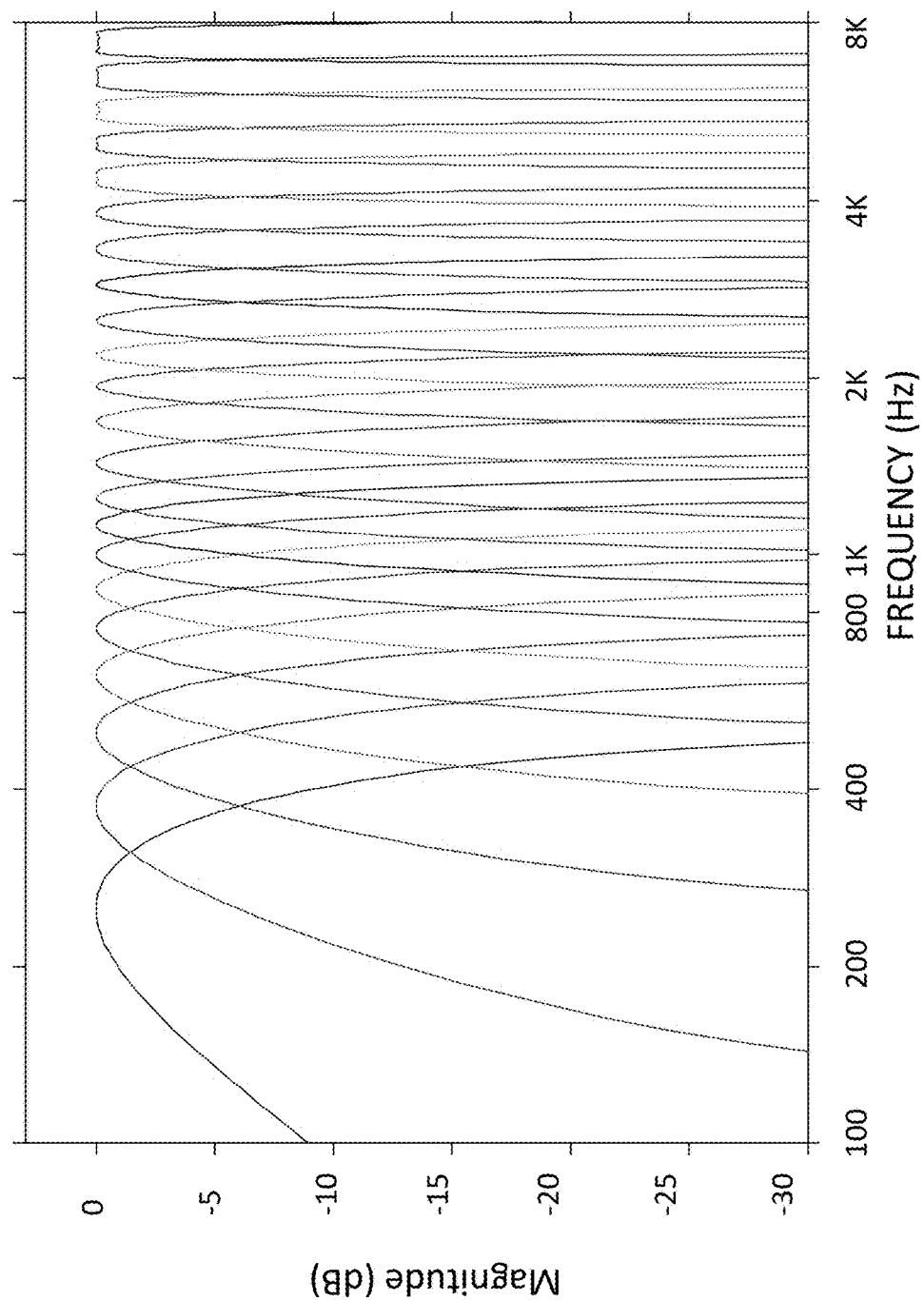
FIG. 2 presents an exemplary frequency band distribution according to an exemplary prosthesis to which the teachings detailed herein can be applicable.

FIG. 2 shows an example of an input acoustic signal being allocated by a filter bank of a sound processor into 22 channels. More specifically, FIG. 2 depicts an example of frequency allocation applied by the sound processor of prosthesis 200, with frequency bands labelled 1 to 22 from low-to-high frequency. In the standard cochlear implant sound coding strategy, the bands are allocated to electrodes. In acoustic plus electric coding, one or more consecutive low frequency bands are allocated to acoustic channels and the remaining bands are allocated to electrodes. The selection of bands for the acoustic channels is based on whether useful information can be delivered acoustically to the individual via amplification. In at least some exemplary embodiments, because of the nature of the hearing loss, the residual hearing is better in the lower frequencies than in the higher frequencies. The teachings detailed herein are directed towards determining what frequency bands to allocate towards acoustic hearing, and what frequency bands to allocate towards electric hearing.

It is noted that the allocation presented in FIG. 2 is by way of example only and not by way of limitation. In an exemplary embodiment, more or fewer channels will be present. By way of example only and not by way of limitation, in some limitations, there can be 14, 15, 16, 17, 18, 19, 20, 21, 22, 23, 24, 25, 26, 27, 28, 29 or 30 channels, or more. Moreover, even for a 22 channel system, some electrodes may not be used, and thus those channels will drop out and or the frequency allocation will be shifted to other channels. Accordingly, the allocation represented in FIG. 2 is for conceptual purposes with respect to some embodiments.

In at least most exemplary embodiments detailed herein, the allocation of bands to acoustic hearing and electric hearing will be directed towards allocating consecutive/ contiguous band groups. That is, in an exemplary embodiment, bands 1, 2, and 3 can be allocated to acoustic hearing, and bands 4 to 22 can be allocated to electric hearing. Alternatively, bands 1 to 4 can be allocated to acoustic hearing, and bands 5 to 22 can be allocated to electric hearing. Thus, in at least most embodiments, there will not be a scenario where, for example, bands 1, 2, 3, and 5 are allocated to acoustic hearing, and bands 4 and 6 to 22 are allocated to electric hearing, as those are not consecutive and contiguous band groups. As will be understood, in at least some exemplary embodiments, the bands to be allocated to acoustic channels (where "channels" is used here in a generic manner—this could be channels of the signal processor that are supplied to the ITE device to evoke an amplified acoustic hearing percept, or generically bands left for normal hearing where the prosthesis does not include acoustic hearing amplification) are consecutive bands from low to high frequency, and the bands allocated to electric channels are consecutive bands from high to low frequency. According to the teachings detailed herein, at least some exemplary embodiments provide for a method of developing a prescription to determine which bands to allocate to acoustic channels in which bands to allocate to electric channels.

Figure 3:
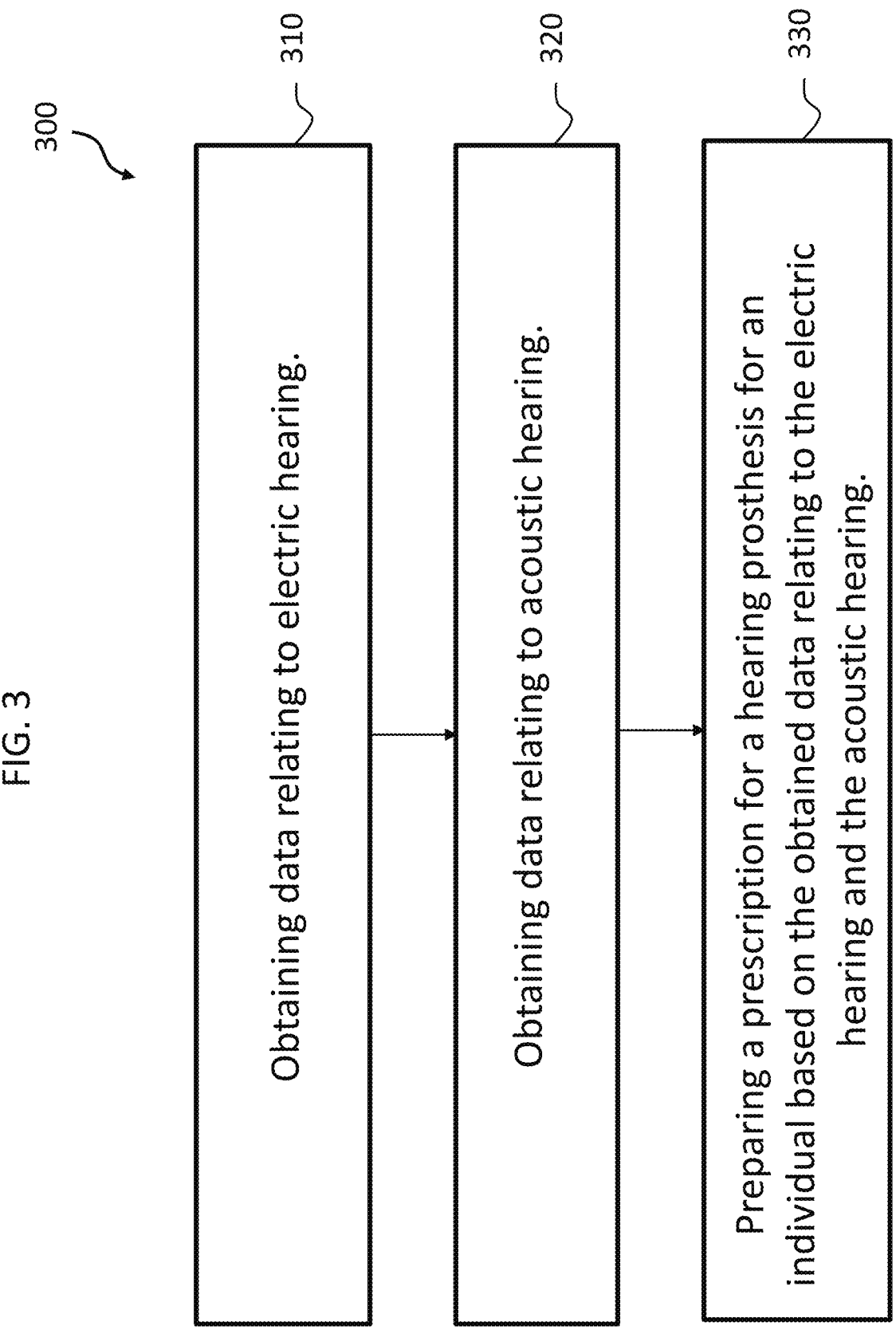
FIG. 3 presents an exemplary flowchart for an exemplary method according to an exemplary embodiment.

FIG. 3 presents an exemplary flowchart for an exemplary method according to an exemplary embodiment that can be utilized in some exemplary scenarios. FIG. 3 presents a flowchart for an exemplary method 300, which method includes method action 310, which comprises obtaining data relating to electric hearing. This can be done by obtaining normative data based on a statistically significant population. This is distinguished from obtaining data relating to subjective data or otherwise based on subjective data with respect to the recipient, as would result when executing a fitting process of the like of the recipient. Again, the teachings detailed herein are directed towards developing a prescription for the recipient prior to implantation of the cochlear implant, or at least prior to the first fitting session. The techniques for developing the data relating to electric hearing will now be described, which data can be used in method 300.

For electric stimulation, normative data from cochlear implant users is obtained. These data can include mean and/or median levels of performance, with measures of between-subject variation. For example, standard deviation, 25% and 75% quartiles, or other measures of confidence intervals can be utilized. Any statistical manipulation technique to include and/or exclude data that has utilitarian value can be utilized in at least some exemplary embodiments. In this regard, the teachings detailed herein are exemplary in nature and can be modified so as to refine the teachings detailed herein.

In an exemplary embodiment, a statistically significant group of cochlear implant users are subjected to testing to determine the impact of given frequency bands on speech understanding, and a function of the impact of those frequency bands, based on performance, is constructed. More specifically, in this exemplary embodiment, the testing entails progressively deactivating, in a consecutive, manner channels of the cochlear implant starting at the lowest frequency band, and maintaining the deactivation of the frequency bands when moving to the next frequency band to deactivate, so as to determine contributions of consecutive and cumulative frequency bands, from low to high frequency. Such contributions of consecutive and cumulative frequency bands, from low to high frequency, can be given by the following equations:

$$EB_1 = SI_{1 \to 22} - SI_{2 \to 22} \quad (1.1)$$

$$EB_{1 \to 2} = SI_{1 \to 22} - SI_{3 \to 22} \quad (1.2)$$

$$EB_{1 \to 3} = SI_{1 \to 22} - SI_{4 \to 22} \quad (1.3)$$

And so on, where EB is the electrode allocated to a frequency band, and bands are numbered 1 to 22 from low to high frequency, as per FIG. 2, and SI=speech information transmitted.

In an exemplary embodiment, SI is an index of performance such as the SII, score on a standardized speech test, or another applicable test. By way of example only and not by way of limitation, in an exemplary embodiment, the SI can be obtained by providing hearing tests to recipients of cochlear implants according to the SII (Speech Intelligibility Index) per ANSI S3.5-1997—Methods For Calculation Of The Speech Intelligibility Index (1997). In an exemplary embodiment, the hearing tests can be implemented in accordance with the teachings of "The relationship between speech perception and electrode discrimination in cochlear implantees," written by Belinda A. Henry et al, published in the Journal Acoust. Soc. Am. 108 (3), Pt. 1, September 2000, as would be modified so as to implement the teachings detailed herein. In an exemplary embodiment, the hearing tests can be provided in the manner provided to obtain the data for that article, save again for the modifications so as to implement the teachings detailed herein. In this regard, by way of example only and not by way of limitation, in an exemplary embodiment, the tests utilized to develop the data of FIGS. 4 and 5 can utilize so-called "CNC" words, as was done in the aforementioned article. In this regard, the tests utilized to obtain the data for FIGS. 4 and 5 can correspond to that associated with FIG. 1 of the article, as modified according to the teachings detailed herein, and the results can correspond to that of FIG. 2 of the article, albeit with different results owing to the fact that the tests are different.

Another example of a test that can be applied to develop an SI score that can be modified to implement the teachings detailed herein can correspond to that that which utilizes monosyllabic words (consonant—vowel—consonant), such as "dog," such as detailed by way of example only and not by way of limitation, in the article 'A frequency importance function for a new monosyllabic word test," to Henry, B. A., McDermott, H. J., McKay, C. M., James, C. J., and Clark, G. M., published in the Journal Aust. J. Audiol. 20, 79-86 in 1998. Still further, another example of a test that can be applied to develop an SI score that can be modified to implement the teachings detailed herein can correspond to that which utilizes familiar sentences (e.g., the cat sat on the mat), such as detailed, by way of example only and not by way of limitation, in the article "The BKB/A (Bamford-Kowal-Bench/Australian Version) Sentence Lists for Hearing-impaired Children," by Bench, R. J., and Doyle, J. M., published by La Trobe University, Victoria.

Any standardized (or non-standardized if such has utilitarian value) speech test that can be utilized to implement the teachings detailed herein to develop data for the data relating to the electric hearing can be utilized in at least some exemplary embodiments.

In this exemplary embodiment, the relative contribution of the lowest frequency band (1) is the difference in SI between a MAP with all bands enabled (1→22)—a map for the cochlear implant, whether such is part of a multimodal prosthesis or not) and a MAP with the electrode corresponding to band 1 removed (2→22).

The relative contribution of the lowest two bands (1→2) is the difference in SI between a MAP with all bands enabled (1→22) and a MAP with electrodes corresponding to bands 1 and 2 removed (3→22). The relative contribution of the lowest three bands (1→3) is the difference in SI between a MAP with all bands enabled (1→22) and a MAP with electrodes corresponding to bands 1, 2, and 3 removed (4→22).

The general form of the contribution is:

$$EB_{1\rightarrow n}=SI_{1\rightarrow 22}-SI_{(n+1)\rightarrow 22} \quad (2)$$

Where n is the band number.

Performance is also sensitive to sensation level as cochlear implant recipients have lower scores for soft speech than for speech presented at conversational level. Incorporating sensation level into (2):

$$EB(SL_e)_{1\rightarrow n}=(SI_{1\rightarrow 22}\times SL_e)-(SI_{(n+1)\rightarrow 22}\times SL_e) \quad (3)$$

Where $SL_e$ is a scaling factor for sensation level; between 0 and 1 for example.

Sensation level is related to presentation level:

$$SL_e=f_e(APR) \quad (4)$$

Where APR is the acoustic presentation level in dB, and the function ($f_e$) is the effect of cochlear implant signal processing.

Figure 4:
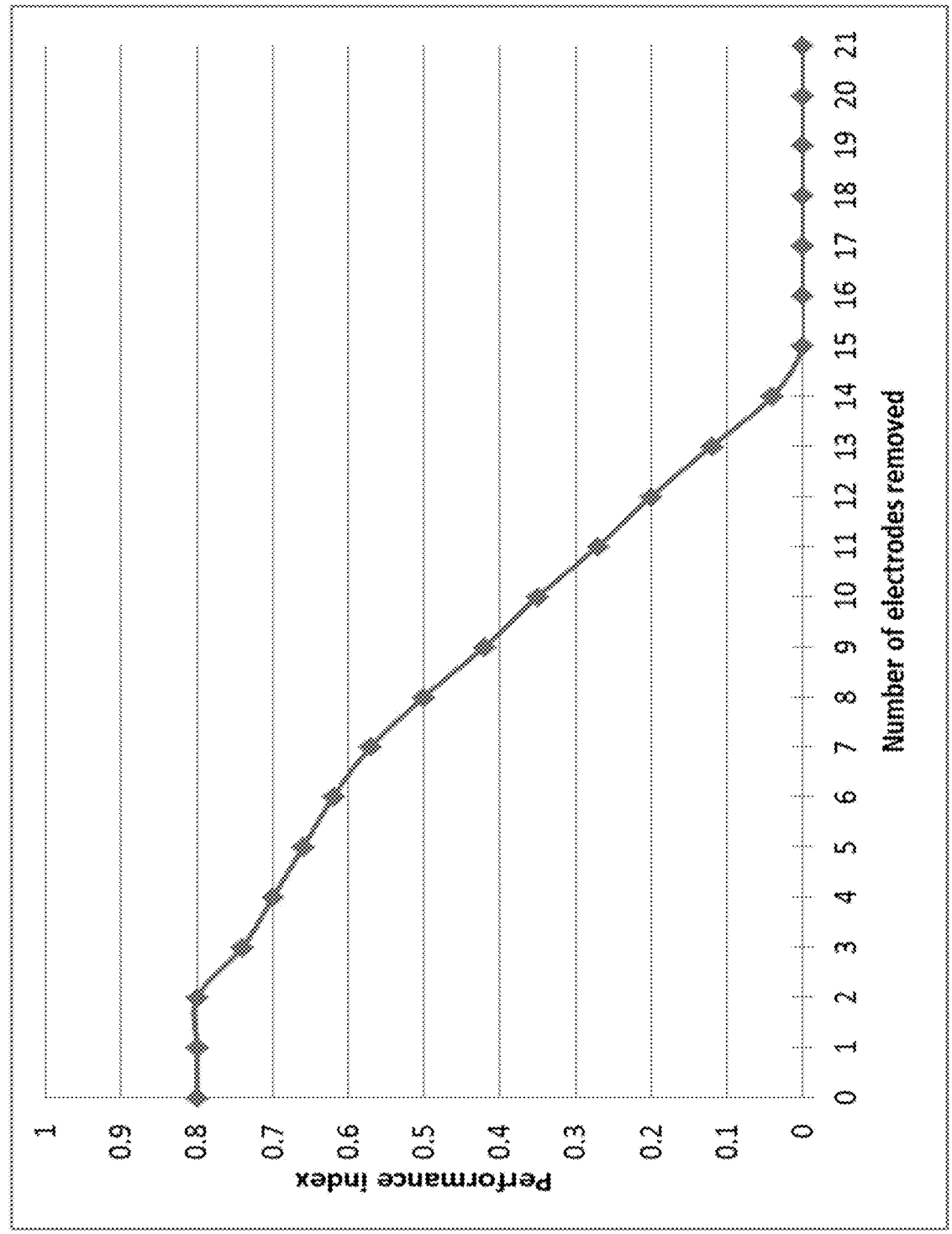
FIG. 4 presents a graph of exemplary data according to an exemplary embodiment.

Based on the results of the above, a function of performance relative to the number of consecutive bands removed is constructed for the cochlear implant user. FIG. 4 shows an exemplary function that results by the progressive deactivation of the electrode channels, from low to high frequency (e.g., 0 means no electrodes (i.e., electrode channels) are removed, 1 means that the electrode (electrode channel) corresponding to the lowest frequency is removed, but no others, 2 means that the electrodes corresponding to the lowest two frequencies are removed, but no others, three means that the electrodes corresponding to the lowest three frequencies are removed, but no others, etc.). The vertical axis is the performance index of the aforementioned speech intelligibility tests unitized from 0 to 1. Again, it is noted that in some alternate embodiments, other types of tests can be utilized.

To be clear, the following technique can be used in some exemplary embodiments, where band 1 constitutes the lowest frequency band, and each band thereafter is a higher frequency band than the prior band (e.g., band 2 is higher than 1, band 3 is higher than bands 2 and 1, etc.).

Apply hearing test with all frequency bands active.

Apply hearing test with frequency band 1 inactive/disabled, and all others active.

Apply hearing test with frequency bands 1 and 2 inactive/disabled, and all others active.

Apply hearing test with frequency bands 1-3 inactive/disabled, and all others active.

Apply hearing test with frequency bands 1-4 inactive/disabled, and all others active.

Apply hearing test with frequency bands 1-5 inactive/disabled, and all others active.

Apply hearing test with frequency bands 1-6 inactive/disabled, and all others active.

Apply hearing test with frequency bands 1-7 inactive/disabled, and all others active.

Apply hearing test with frequency bands 1-8 inactive/disabled, and all others active.

Apply hearing test with frequency bands 1-9 inactive/disabled, and all others active.

Apply hearing test with frequency bands 1-10 inactive/disabled, and all others active.

Apply hearing test with frequency bands 1-11 inactive/disabled, and all others active.

Apply hearing test with frequency bands 1-12 inactive/disabled, and all others active.

Apply hearing test with frequency bands 1-13 inactive/disabled, and all others active.

Apply hearing test with frequency bands 1-14 inactive/disabled, and all others active.

Apply hearing test with frequency bands 1-15 inactive/disabled, and all others active.

Apply hearing test with frequency bands 1-16 inactive/disabled, and all others active.

Apply hearing test with frequency bands 1-17 inactive/disabled, and all others active.

Apply hearing test with frequency bands 1-18 inactive/disabled, and all others active.

Apply hearing test with frequency bands 1-19 inactive/disabled, and all others active.

Apply hearing test with frequency bands 1-20 inactive/disabled, and all others active.

Apply hearing test with frequency bands 1-21 inactive/disabled, and all others active.

As can be seen from the figures, as more consecutive electrodes coding low frequencies are removed, performance decreases. In this example, performance begins to decrease when the first 3 low frequency electrodes are removed, but not when the first 2 low frequency electrodes are removed. As contribution is the opposite of decrease, FIG. 5 plots the same data to show the contribution of the individual bands (the diamond data points) and the cumulative contribution (the square data points), ordered from low to high frequency.

The above processes are repeated for other cochlear implant users, which users can be relevant to the given recipient in a statistical manner. By way of example only and not by way of limitation, the above processes are repeated for 10, 15, 20, 25, 30, 35, 40, 45, 50, 55, 60, 65, 70, 75, 80, 85, 90, 95, or 100, or more cochlear implant users, or any other number of cochlear implant users which can be utilized as a representative of an accurate statistical sample or the like, and the results are normalized, and a normalized function is developed. For the purposes of discussion herein, the normalized functions will be treated as that which corresponds to the functions of FIGS. 4 and 5. Of course, in practice, the functions can be different. These functions are but for exemplary purposes.

Figure 5:
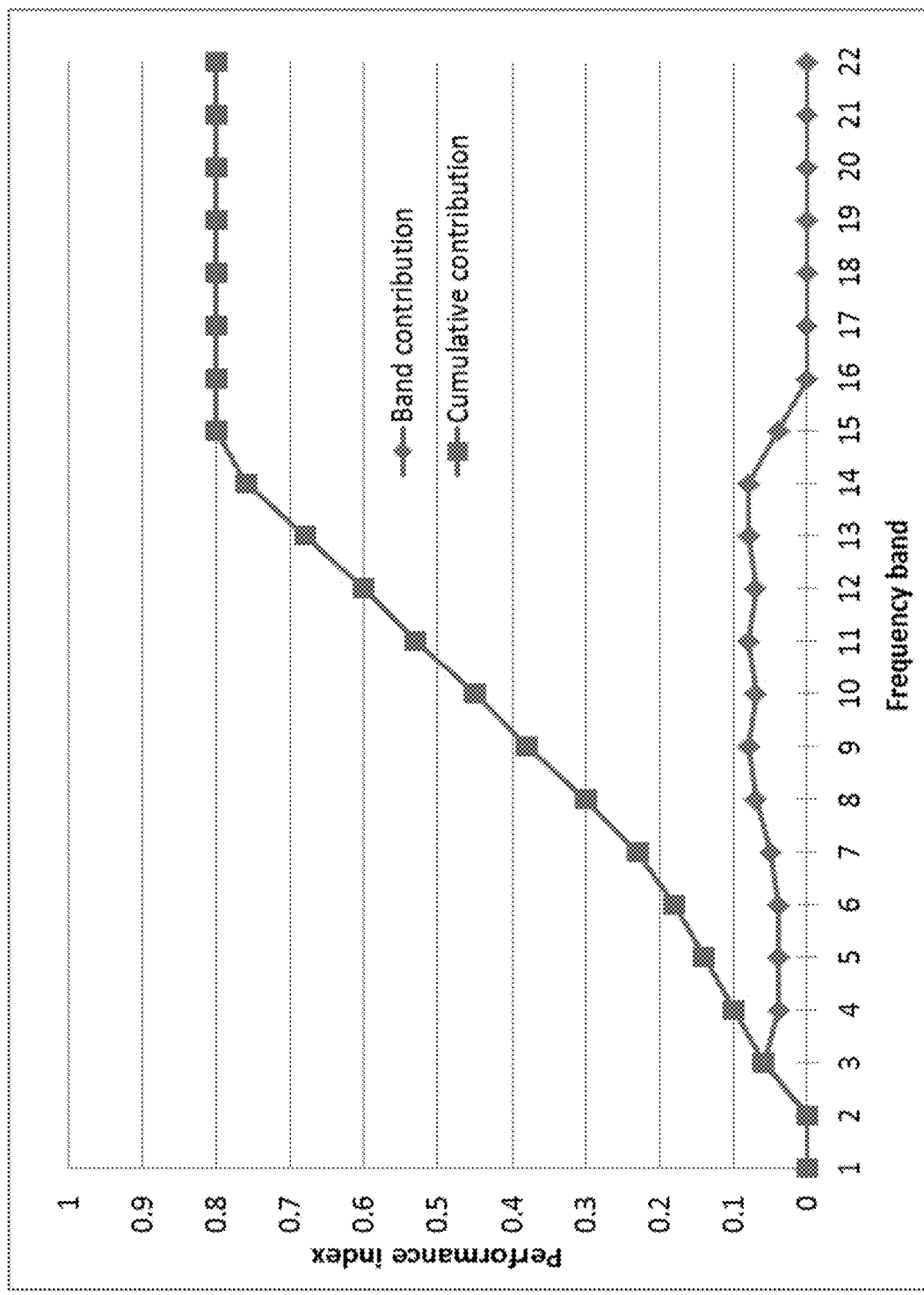
FIG. 5 presents another graph of exemplary data according to an exemplary embodiment.

Accordingly, method action 310 can entail obtaining a function corresponding to that of FIG. 4 and/or FIG. 5.

Method 300 further includes method 320, which includes the action of obtaining data relating to acoustic hearing. This can be done by obtaining normative data based on a statistically significant population, but can also be done by obtaining subject data relating to the specific recipient, which can be obtained prior to the implantation of the cochlear implant, or prior to activation thereof, or prior to the first fitting session fitting the cochlear implant to the recipient. It is noted that this data can be based on normal hearing without amplification, or can be based on the use of a hearing prosthesis such as an acoustic hearing aid (e.g., the non-cochlear implant portion of the prosthesis 200). Again, the teachings detailed herein are directed towards developing a prescription for the recipient prior to implantation of the cochlear implant, or at least prior to the first fitting session. The techniques for developing the data relating to acoustic hearing will now be described, which data can be used in method 300.

For acoustic stimulation, in at least some exemplary embodiments, the same process applied as detailed above for the electric hearing is also applied, but the frequency band removal order is reversed. That is, frequency bands are deactivated starting from the highest frequency band and working down to the lowest frequency band. Also, as noted above, the source of data can be normative data, or can be based on the individual who is to receive the cochlear implant. There can be utilitarian value with respect to utilizing individual data in that the cross-over-frequency can be targeted to the individual. There can be utilitarian value with respect to utilizing normative data in that for a given hearing loss, an estimate of the cross-over frequency is calculated and no individual measurements are needed or otherwise utilized.

For acoustic stimulation functions based on normative data, normative data for acoustic hearing aid users is obtained and/or normative data for hearing impaired persons not utilizing an acoustic hearing aid is obtained (in some exemplary embodiments, an acoustic hearing aid will not be part of the prosthesis 200 (e.g., the prosthesis will not be a multimodal prosthesis, but instead will be a cochlear implant prostheses), while in other embodiments, data can be utilized to analyze the data for persons not utilizing an acoustic hearing aid to determine or otherwise estimate the change in score of a hearing test will result from the application of an acoustic hearing aid). As was the case with the electric hearing, these data can include mean and/or median levels of performance, with measures of between-subject variation. For example, standard deviation, 25% and 75% quartiles, or other measures of confidence intervals can be utilized. Any statistical manipulation technique to include and/or exclude data that has utilitarian value can be utilized in at least some exemplary embodiments. In this regard, the teachings detailed herein are exemplary in nature and can be modified so as to refine the teachings detailed herein.

In an exemplary embodiment, a statistically significant group of hearing impaired persons are subjected to testing to determine the impact of given frequency bands on speech understanding, and a function of the impact of those frequency bands, based on performance, is constructed. More specifically, in this exemplary embodiment, the testing entails progressively eliminating in a consecutive manner frequency bands starting at the highest frequency band, and maintaining the elimination of the frequency bands when moving to the next frequency band to eliminate, so as to determine contributions of consecutive and cumulative frequency bands, from high to low frequency. It is noted that with respect to the embodiments where an acoustic hearing aid is utilized, the channels associated with those frequency bands can be deactivated in a manner analogous to the deactivation of the channels associated with the cochlear implant. With respect to embodiments where no acoustic hearing aid is utilized, sound content applied to the recipient can be such that frequency bands are removed from the sound. By way of example only and not by way of limitation, an adjustable bandpass filter can be placed in between and output of a sound generator and a speaker, which can be used to progressively eliminate frequencies from higher to lower. Any device, system, and/or method that will enable the acoustic data to be developed or otherwise obtained can be utilized in at least some exemplary embodiments, as long as such has utilitarian value with respect to implementing the teachings detailed herein and/or variations thereof.

Contributions of consecutive and cumulative frequency bands, from high to low frequency, can be given by the following equations:

$$AB_{22} = SI_{22 \to 1} - SI_{21 \to 1} \tag{5.1}$$

$$AB_{22 \to 21} = SI_{22 \to 1} - SI_{20 \to 1} \tag{5.2}$$

$$AB_{22 \to 20} = SI_{22 \to 1} - SI_{19 \to 1} \tag{5.3}$$

And so on, where AB is the acoustic channel allocated to a frequency band, and bands are numbered 1 to 22 from low to high frequency, as per FIG. 2, and SI=speech information transmitted.

As with the function developed for electric hearing detailed above, in an exemplary embodiment, SI is an index of performance such as the SII, score on a standardized speech test, or another applicable test. By way of example only and not by way of limitation, in an exemplary embodiment, the SI can be obtained by providing hearing tests to recipients of cochlear implants according to the SII (speech Intelligibility Index) per ANSI S3.5-1997—Methods For Calculation Of The Speech Intelligibility Index (1997).

In an exemplary embodiment, the hearing tests can be implemented in accordance with at least one or more or all of the teachings of "Speech recognition of hearing-impaired listeners: Predictions from audibility and the limited role of high-frequency amplification," written by Teresa Y. C. Ching, et al, published in the J. Acoust. Soc. Am. 103 (2), February 1998, as would be modified so as to implement the teachings detailed herein. In an exemplary embodiment, the hearing tests can be provided in the manner provided to obtain the data for that article, save again for the modifications so as to implement the teachings detailed herein. In this regard, by way of example only and not by way of limitation, in an exemplary embodiment, the tests utilized to develop the data of FIGS. 7 and 8 can utilize so-called "BKB" sentences, as was done in the aforementioned article, albeit with different results owing to the fact that the tests are different.

Any standardized (or non-standardized if such has utilitarian value) speech test that can be utilized to implement the teachings detailed herein to develop data for the data relating to the electric hearing can be utilized in at least some exemplary embodiments. It is noted that the techniques applied to develop the data for the Henry article can be applied, as modified to execute the teachings detailed herein, to develop the data for the non-electrical hearing, and the techniques applied to develop the data for the Ching article can be applied, as modified to execute the teachings detailed herein, to develop the data for the electric hearing.

Another example of a test that can be applied to develop an SI score that can be modified to implement the teachings detailed herein can correspond to that that which utilizes monosyllabic words (consonant—vowel—consonant), such as "dog," such as detailed by way of example only and not by way of limitation, in the article 'A frequency importance function for a new monosyllabic word test," to Henry, B. A., McDermott, H. J., McKay, C. M., James, C. J., and Clark, G. M., published in the Journal Aust. J. Audiol. 20, 79-86 in 1998. Still further, another example of a test that can be applied to develop an SI score they can be modified to implement the teachings detailed herein can correspond to that which utilizes familiar sentences (e.g., the cat sat on the mat), such as detailed by way of example only and not by way of limitation, in the article "The BKB/A (Bamford-Kowal-Bench/Australian Version) Sentence Lists for Hearing-impaired Children," by Bench, R. J., and Doyle, J. M., published by La Trobe University, Victoria.

It is noted that in at least some embodiments, the test used for electric hearing is the same as that use for acoustic hearing.

In this exemplary embodiment, the relative contribution of the highest frequency band (22) is the difference in SI between an acoustic signal with all bands enabled (22→1) and an acoustic signal with the highest frequency band 22 removed (22→1). The relative contribution of the highest two bands (22→21) is the difference in SI between an acoustic signal with all bands enabled (22→1) and an acoustic signal with bands 22 and 21 removed (20→1). The relative contribution of the highest three bands (19→1) is the difference in SI between an acoustic signal with all bands enabled (22→1) and an acoustic signal corresponding to bands 22, 21 and 20 removed (19→1).

The general form of the contribution is:

$$AB_{22 \to n} = SI_{22 \to 1} - SI_{(n-1) \to 1} \tag{6}$$

Where n is the band number.

In at least some exemplary embodiments, performance is also sensitive to sensation level because of the effects of hearing loss and acoustic gain applied to overcome the hearing loss. Incorporating sensation level into (6):

$$AB(SL_a)_{22 \to n} = (SI_{22 \to 1} \times SL_a) - (SI_{(n-1) \to 1} \times SL_a) \tag{7}$$

Where $SL_a$ is a scaling factor for sensation level; between 0 and 1 for example.

Sensation level is related to presentation level:

$$SL_a = f_a(APR) \tag{8}$$

Where APR is the acoustic presentation level in dB, and the function ($f_a$) is the effect of hearing loss and acoustic gain.

In at least some exemplary embodiments, the contributions of all cumulative frequency bands in (7) are not measured. This can be because in at least some scenarios, there are limitations on how much acoustic gain can be delivered. The acoustic amplification region is defined as the frequency range where acoustic amplification has the potential to provide useful information, such as speech, to the recipient. Beyond this frequency range there will be no benefit from acoustic amplification. There are several related methods for defining this region, for example by reference to hearing threshold (9) or by whether the acoustic signal delivery system is able to deliver the prescribed gain without saturation (10). Any method for defining this region that can have utilitarian value can be utilized in at least some exemplary embodiments. For example the teachings presented in the 2012 article by Dillon, entitled, Hearing Aids, by Thieme Publishers, New York, can be utilized in some embodiments.

For acoustic frequency bands ordered from low to high frequency, the highest frequency band by reference to hearing threshold is found utilizing the following:

$$F(\text{Hz}) \text{ where } x\text{dB}(HL) < n\text{dB}(HL) \tag{9}$$

Where F(Hz) is frequency in Hz, xdB(HL) is hearing threshold in dB at F(Hz), and ndB(HL) is the pre-defined criterion at F(Hz).

Determining whether the acoustic system is able to deliver the prescribed gain without saturation can be determined utilizing the following:

$$F(\text{Hz}) \text{ where } (x\text{dB} + y\text{dB}) < s\text{dB} \tag{10}$$

Where F(Hz) is frequency in Hz, xdB is a pre-defined input signal level, ydB is the prescribed hearing aid gain at F(Hz) and sdB is the saturation level or maximum output of the acoustic signal delivery system at F(Hz).

Figure 6:
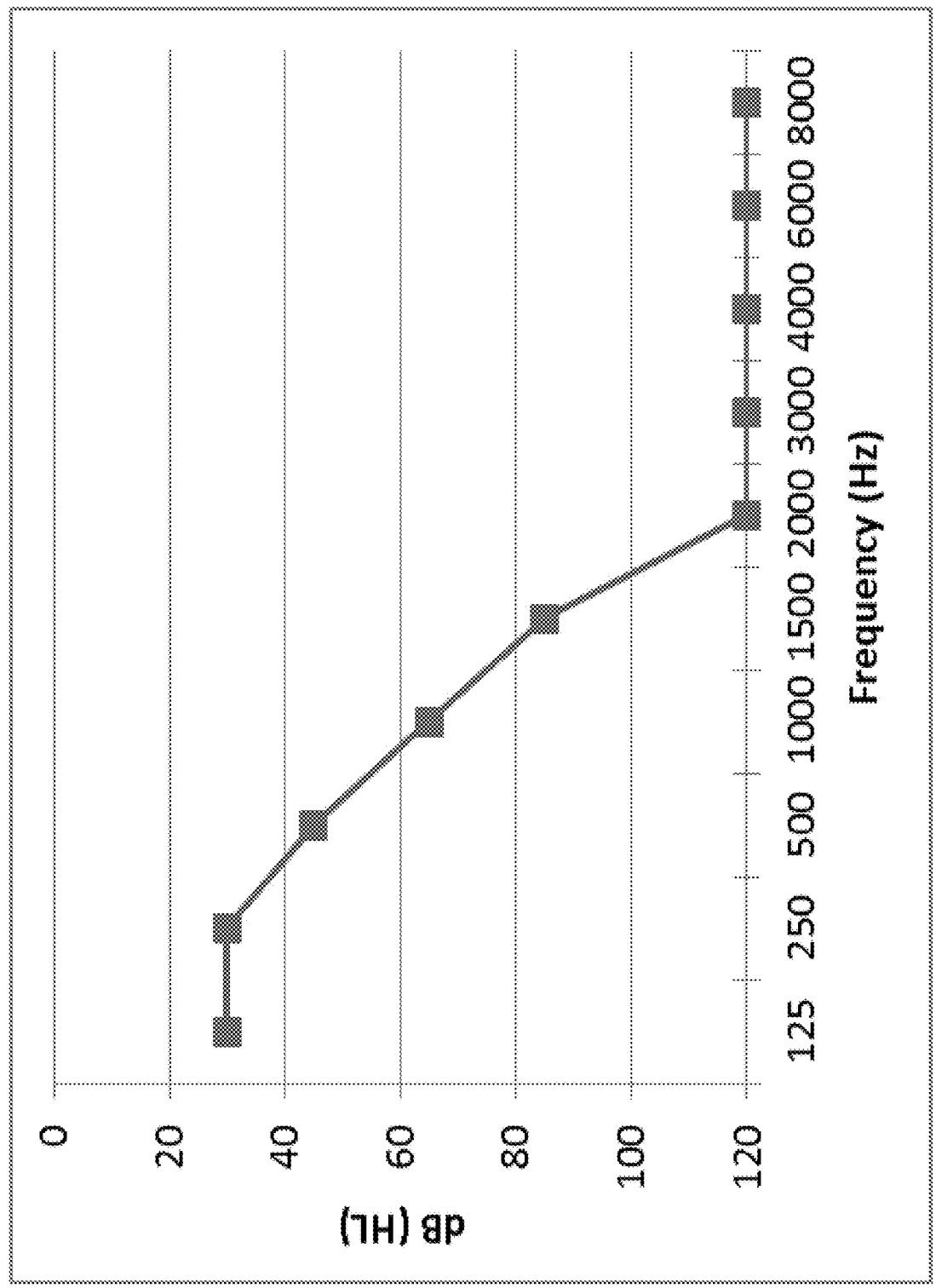
FIG. 6 presents another graph of exemplary data according to an exemplary embodiment.
Figure 7:
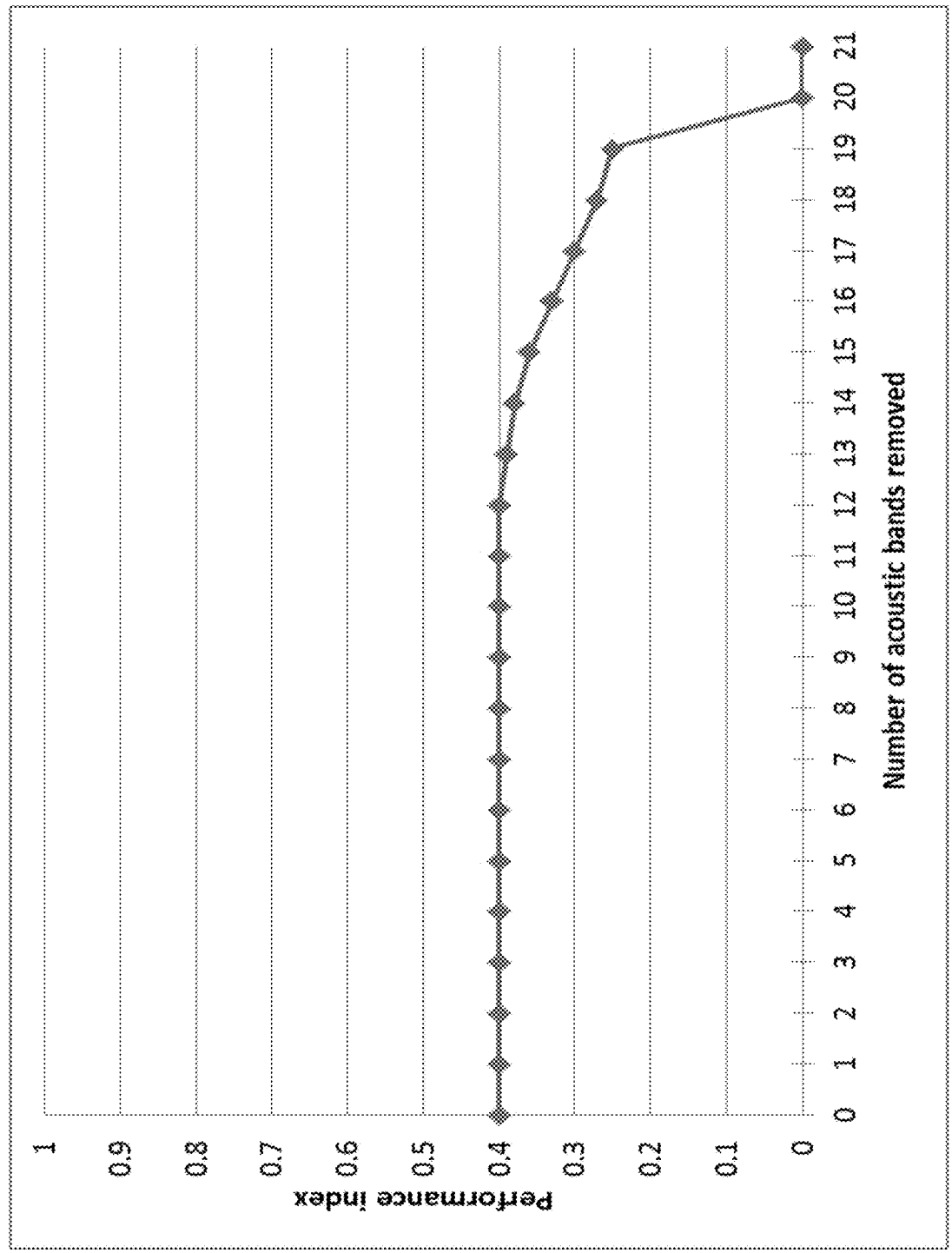
FIG. 7 presents another graph of exemplary data according to an exemplary embodiment.

FIG. 6 shows an example audiogram of a cochlear implant recipient with residual hearing. FIG. 7 depicts an example performance index function that might be obtained from this recipient. FIG. 7 shows an exemplary function that results by the progressive elimination of the frequency bands, from high to low frequency (e.g., 0 means no frequency bands are removed/eliminated, 1 means that the frequency band corresponding to the highest frequency is removed, but no others, 2 means that the frequency bands corresponding to the highest two frequencies are removed, but no others, 3 means that the frequency bands corresponding to the highest three frequencies are removed, but no others, etc.). The vertical axis is the performance index of the aforementioned speech intelligibility tests unitized from 0 to 1. Again, it is noted that in some alternate embodiments, other types of tests can be utilized.

Figure 8:
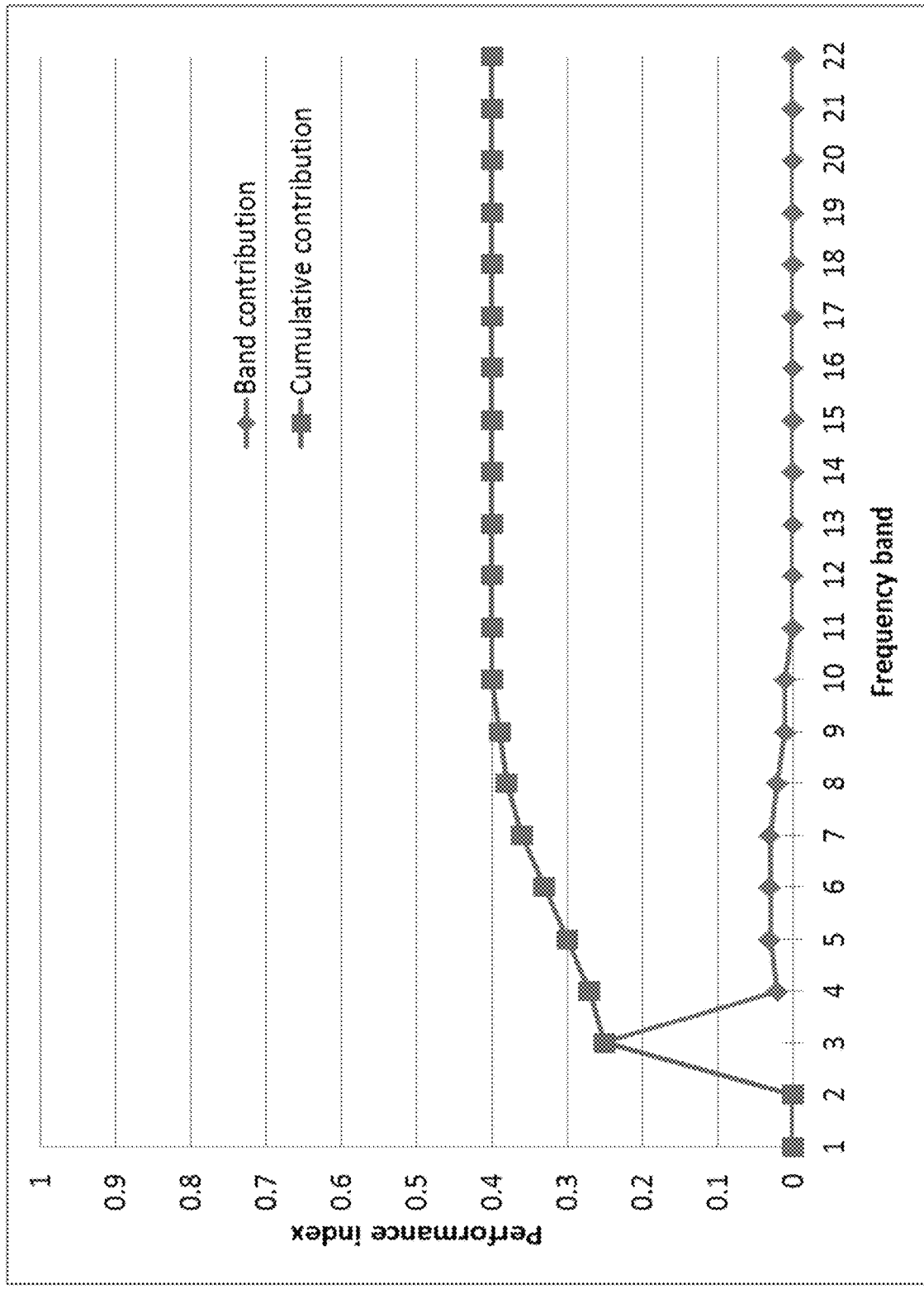
FIG. 8 presents another graph of exemplary data according to an exemplary embodiment.

FIG. 8 plots the same data to show the contribution of the individual bands and the cumulative contribution, ordered from low-to-high frequency, representing a function of performance relative to the number of consecutive bands removed The functions depicted in FIGS. 6-8 can be representative of an individual or can correspond to normalized data, depending on how the teachings detailed herein are applied. As can be seen, performance begins to decline after 12 bands are removed, as contribution is the opposite of decrease.

Accordingly, method action 320 can entail obtaining a function corresponding to that of FIG. 7 and/or FIG. 8.

To be clear, the following technique can be used in some exemplary embodiments, where band 22 constitutes the highest frequency band, and each band below that band is a lower frequency band than the prior band (e.g., band 22 is higher than 21, bands 22 and 21 are higher than 20, etc.).

Apply hearing test with all frequency bands active.

Apply hearing test with frequency band 22 inactive/disabled, and all others active.

Apply hearing test with frequency bands 22-21 inactive/disabled, and all others active.

Apply hearing test with frequency bands 22-20 inactive/disabled, and all others active.
Apply hearing test with frequency bands 22-19 inactive/disabled, and all others active.
Apply hearing test with frequency bands 22-18 inactive/disabled, and all others active.
Apply hearing test with frequency bands 22-17 inactive/disabled, and all others active.
Apply hearing test with frequency bands 22-16 inactive/disabled, and all others active.
Apply hearing test with frequency bands 22-15 inactive/disabled, and all others active.
Apply hearing test with frequency bands 22-14 inactive/disabled, and all others active.
Apply hearing test with frequency bands 22-13 inactive/disabled, and all others active.
Apply hearing test with frequency bands 22-12 inactive/disabled, and all others active.
Apply hearing test with frequency bands 22-11 inactive/disabled, and all others active.
Apply hearing test with frequency bands 22-10 inactive/disabled, and all others active.
Apply hearing test with frequency bands 22-9 inactive/disabled, and all others active.
Apply hearing test with frequency bands 22-8 inactive/disabled, and all others active.
Apply hearing test with frequency bands 22-7 inactive/disabled, and all others active.
Apply hearing test with frequency bands 22-6 inactive/disabled, and all others active.
Apply hearing test with frequency bands 22-5 inactive/disabled, and all others active.
Apply hearing test with frequency bands 22-4 inactive/disabled, and all others active.
Apply hearing test with frequency bands 22-3 inactive/disabled, and all others active.
Apply hearing test with frequency bands 22-2 inactive/disabled, and all others active.

It is noted that by "inactive/disabled," this also includes the scenario where a hearing aid is not being used, but the ambient sound content has been blocked with respect to that frequency band.

With reference again to FIG. 3, method 300 further includes method action 330, which includes the action of preparing a prescription for a multimodal (sometimes referred to as a hybrid) hearing prosthesis for an individual based on the obtained data relating to the electric hearing and the acoustic hearing. In an exemplary embodiment, this entails utilizing data relating to the data presented in FIGS. 4 and/or 5 on the one hand with respect to electric hearing, and on the other hand with respect to FIGS. 7 and/or 8 with respect to acoustic hearing.

Figure 9A:
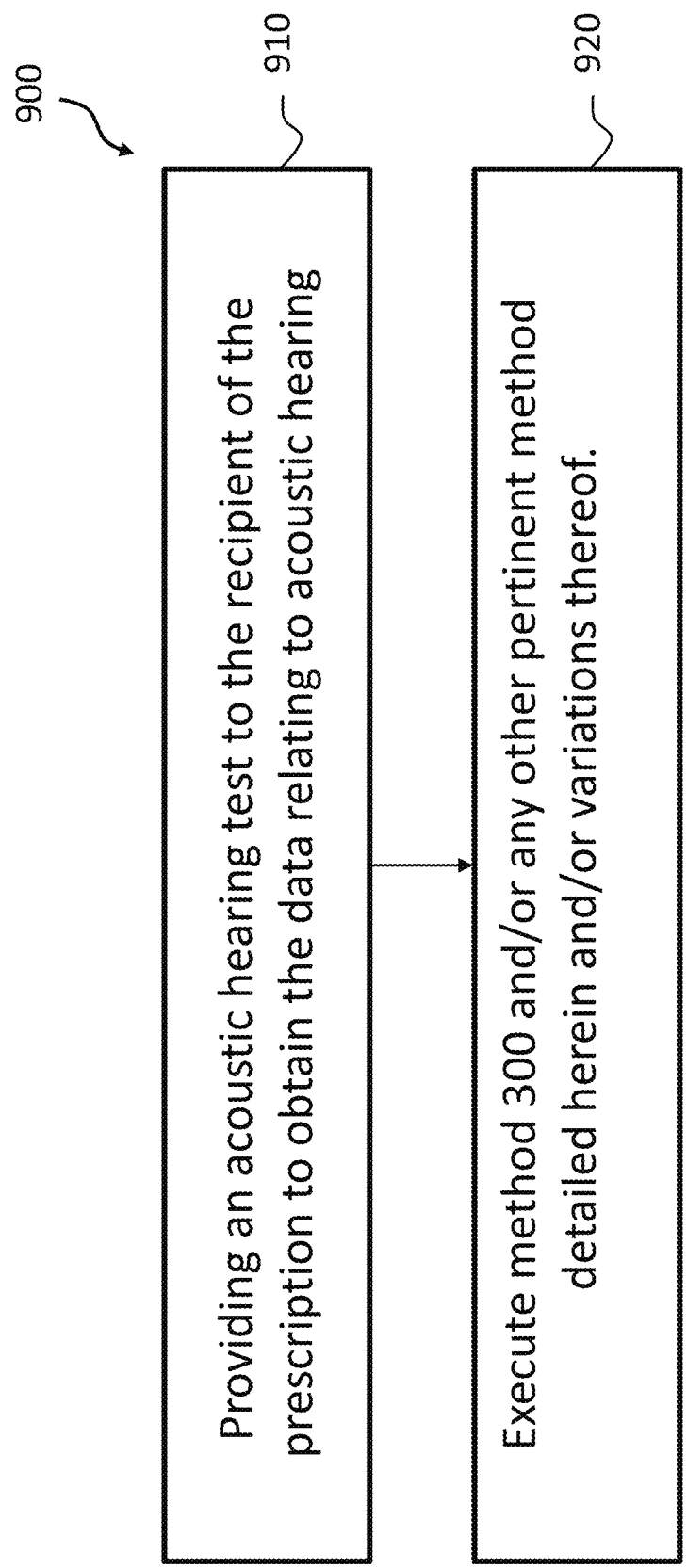
FIG. 9A presents another exemplary flowchart for an exemplary method according to an exemplary embodiment.

As noted above, in some exemplary embodiments, normative data can be utilized to develop the data relating to acoustic hearing utilized in method 300 the other methods detailed herein. That said, as noted above, subjective data can instead be utilized. To this end, FIG. 9A presents an exemplary flowchart for an exemplary method 900. Method 900 includes method action 910, which entails providing an acoustic hearing test to the recipient of the prescription to obtain data relating to acoustic hearing. The acoustic hearing test can be any of the standard acoustic hearing tests that can be modified so as to enable the teachings detailed herein. In an exemplary embodiment, the action of providing the acoustic hearing test includes progressively blocking frequencies falling within frequency bands in a descending manner with the previously blocked frequency bands remaining blocked, thereby obtaining relative contributions to the respective frequency bands for acoustic hearing of the recipient. In an exemplary embodiment, the action of progressively blocking frequencies falling within frequency bands in a descending manner with the previously blocked frequency bands remaining blocked corresponds to the applicable disclosure noted above (those associated with equation 6, etc.). Method 900 further includes method action 920 which entails executing method 300, or any other methods detailed herein, utilizing the results of the acoustic hearing test executed in method action 910 as the basis for the data relating to the acoustic hearing data of method 300.

Figure 9B:
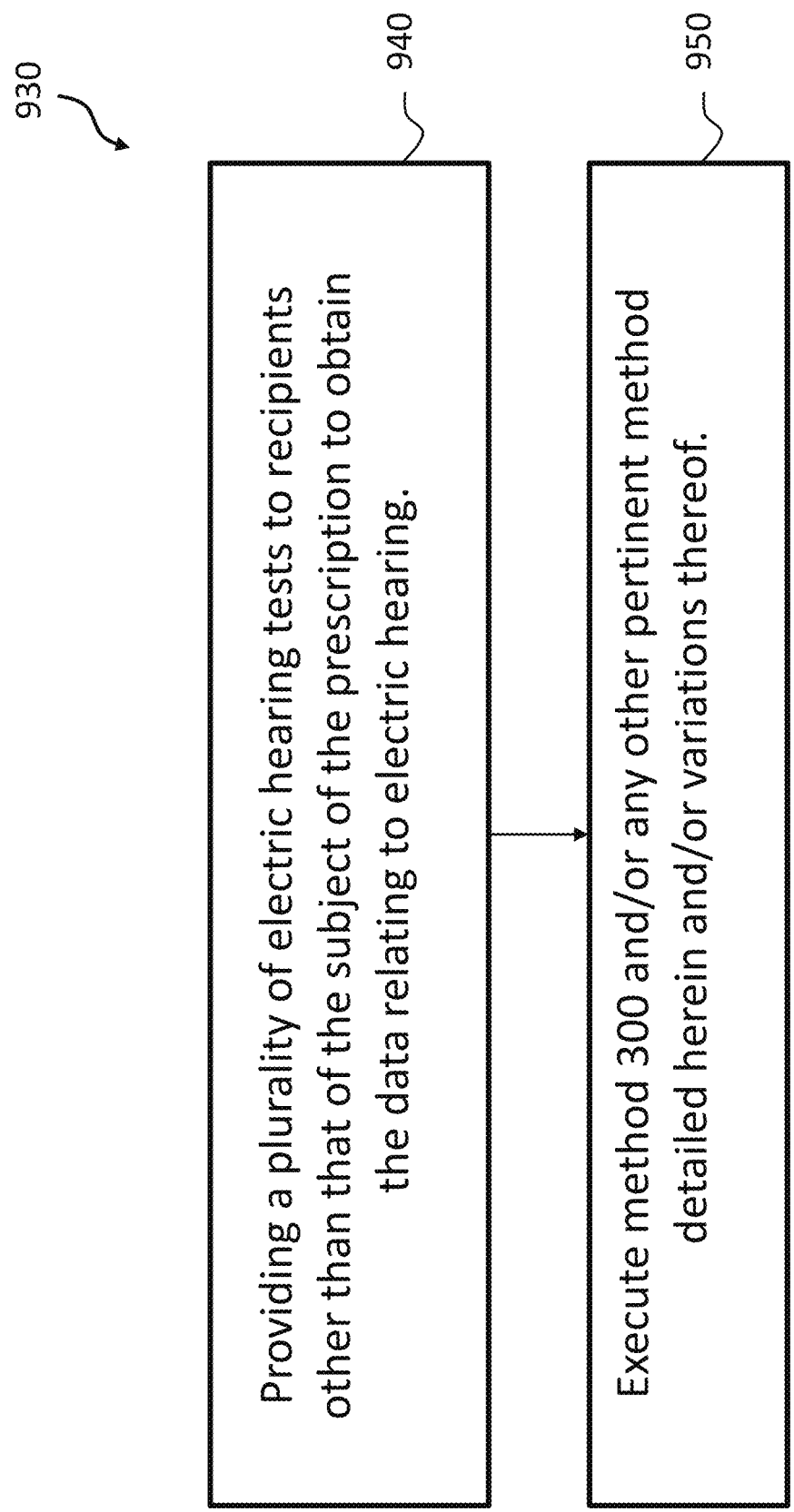
FIG. 9B presents another exemplary flowchart for an exemplary method according to an exemplary embodiment.

Corollary to method 900 is method 930, represented by the flowchart in FIG. 9B. Method 930 includes method action 940, which entails providing a plurality of respective electric hearing tests to respective recipients of cochlear implants, other than that of the subject of the prescription to obtain the data relating to electric hearing. In an exemplary embodiment, the action of providing these hearing tests includes progressively blocking frequencies falling within frequency bands in an ascending manner with the previously blocked frequency bands remaining blocked, thereby obtaining relative contributions of the respective frequency bands for electric hearing. In an exemplary embodiment, the action of progressively blocking frequencies falling within frequency bands with the previously blocked frequency bands remaining blocked corresponds to the applicable disclosure noted above. Method 930 further includes method action 950, which entails executing method 300 and/or any of the other methods detailed herein utilizing the results of method action 940.

Figure 9C:
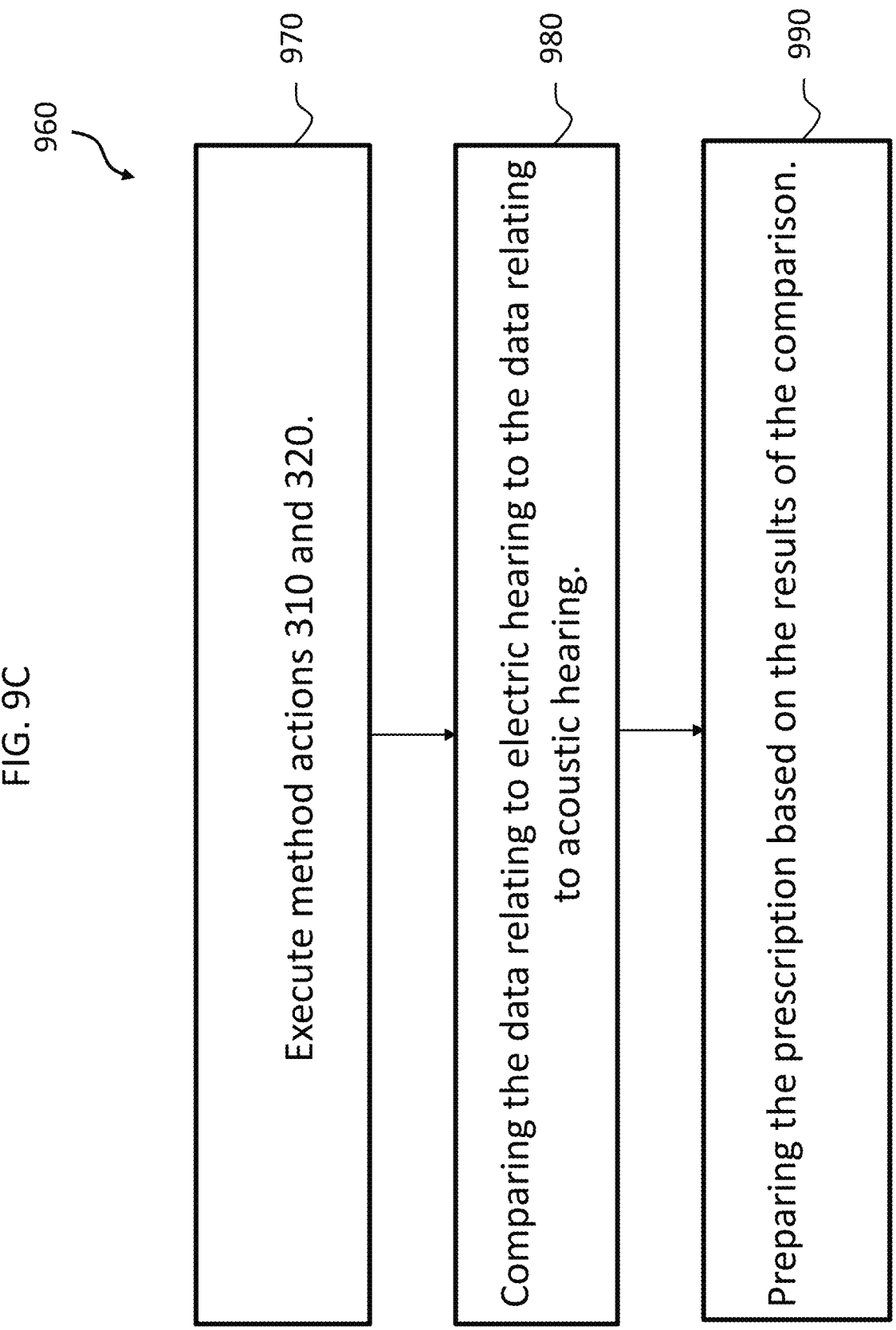
FIG. 9C presents another exemplary flowchart for an exemplary method according to an exemplary embodiment.
Figure 10:
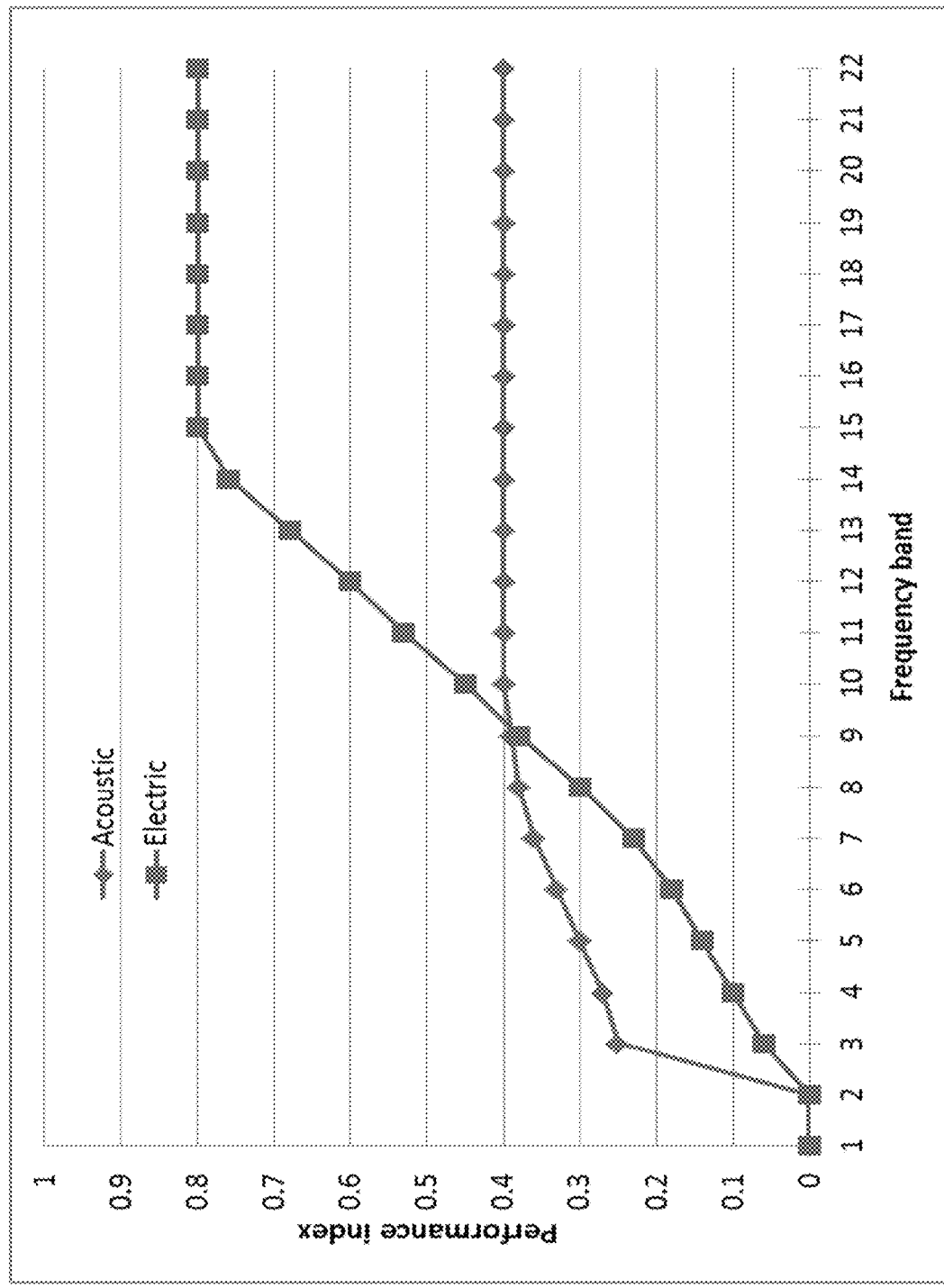
FIG. 10 presents another graph of exemplary data according to an exemplary embodiment.

FIG. 9C presents an exemplary flowchart for an exemplary method 900 according to an exemplary embodiment. Method 960 includes method action 970, which includes executing method actions 310 and 320 of method 300. Method 970 further includes method action 980, which comprises comparing the data relating to electric hearing obtained in method action 310 to the data relating to acoustic hearing obtained in method action 320. FIG. 10 depicts the cumulative contributions of frequency bands for electric and acoustic stimulation (FIGS. 5 and 8, respectively) plotted by band number from low-to-high frequency. FIG. 10 thus represents an exemplary action that can be executed when executing method action 920. In an exemplary embodiment of an analysis with respect to the comparison of method action 920, such analysis would result in a determination that for bands below band 9, acoustic stimulation provides more information than that which results from electric stimulation (electric stimulation without acoustic stimulation, or at least without amplified acoustic stimulation from a traditional conventional hearing aid—more on this below), while for bands above band 9, electric stimulation provides more information than that which results from acoustic stimulation (acoustic stimulation without electric stimulation).

Below presents a general definition of the cross-over frequency, that is, the frequency band to assign to electric stimulation, using (3) and (7):

$$\text{IF } EB(SL_e)_{1 \to n} > AB(SL_a)_{22 \to n} \text{ THEN CF}=n \qquad (11)$$

where CF=cross-over frequency.

In view of FIG. 10 and/or the other detail above, it can be seen that acoustic stimulation could be used for bands 1-9 and electric stimulation for bands 10-22 so as to maximize acoustic hearing, but only where such maximization provides utilitarian value with respect to providing more information/more understanding of speech content than that which results from electrical hearing. Thus, with reference to FIG. 9, the exemplary method 900 includes method action 930, which entails preparing the prescription based on the results of the comparison. In an exemplary embodiment, the prescription would be prepared such that for the user of the cochlear implant having residual hearing, whether that person utilizes a multimodal device or a cochlear implant with natural residual hearing without amplification from a traditional hearing aid, etc., the prescription would indicate that the cochlear implant should provide electrical stimulation for bands 10, 11, 12, 13, 14, 15, 16, 17, 18, 19, 20, 21, and 22, but no others. In an exemplary embodiment where a multimodal prosthesis is utilized, whether such corresponds to an integrated system according to the teachings of FIGS. 1A and 1B above, or whether such corresponds to the utilization of a standalone conventional hearing aid, the prescription could also indicate that the multimodal device should provide acoustic stimulation for bands 1, 2, 3, 4, 5, 6, 7, 8, and 9, but no others (at least with respect to amplification of such bands).

Figure 9D:
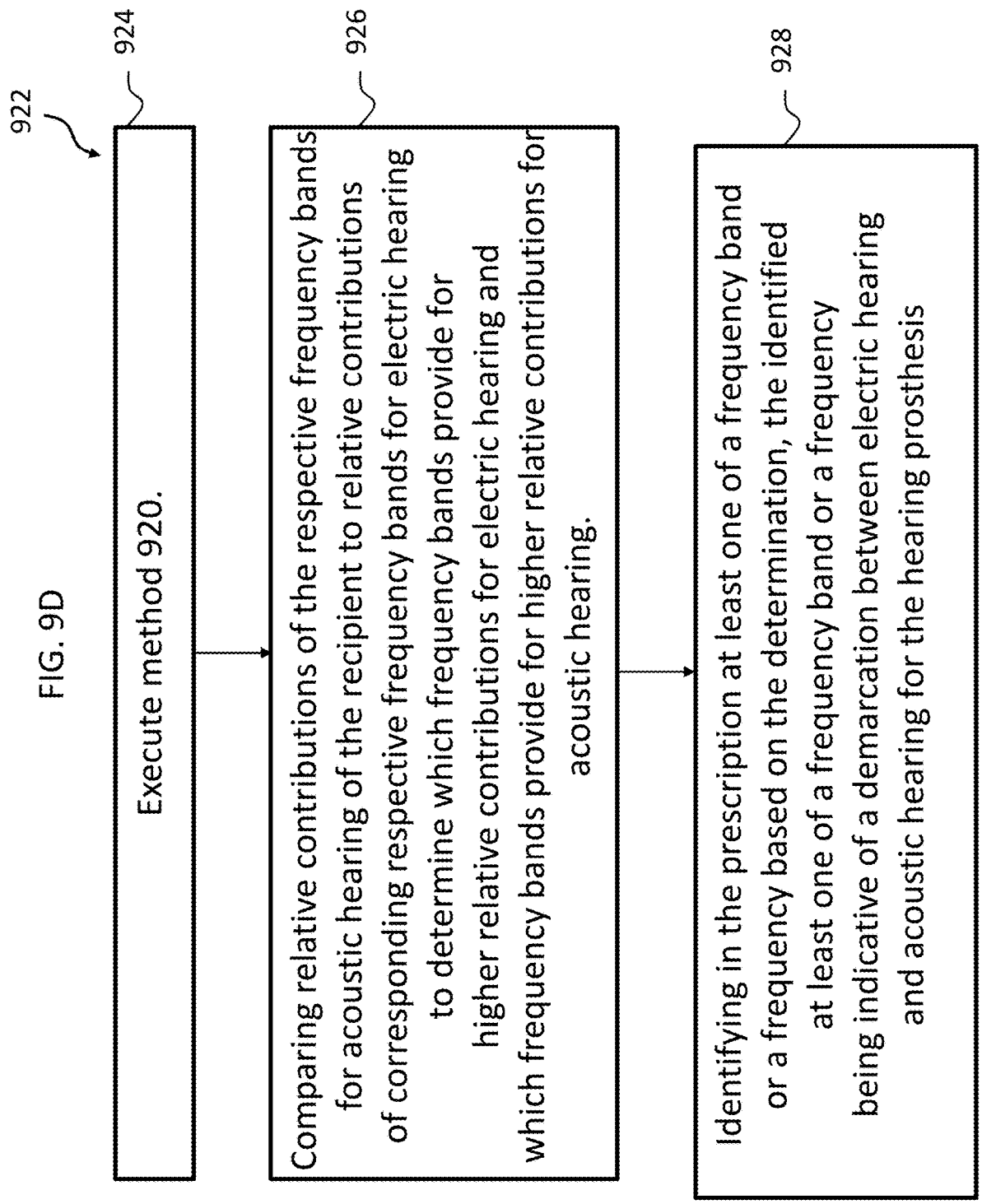
FIG. 9D presents another exemplary flowchart for an exemplary method according to an exemplary embodiment.

FIG. 9D presents another flowchart for an exemplary method 922, which includes method action 924, which entails executing method 920. Method 922 further includes method action 926, which entails comparing relative contributions of the respective frequency bands for acoustic hearing of the recipient to relative contributions of corresponding respective frequency bands for electric hearing to determine which frequency bands provide for higher relative contributions for electric hearing and which frequency bands provide for higher relative contributions for acoustic hearing. Consistent with the teachings detailed above, in an exemplary embodiment, this entails comparing the scores from the standard speech test in the manner detailed above these of the consecutively and progressively and cumulatively eliminating frequency bands. Method 922 further includes method action 928, which entails identifying in the prescription at least one of a frequency band or a frequency based on the determination, the identified at least one of a frequency band or a frequency being indicative of a demarcation between electric hearing and acoustic hearing for the multimodal hearing prosthesis.

It is noted that some exemplary embodiments can be configured so that the in the ear device provides a barrier to sound waves reaching the tympanic membrane, or at least muffles the sound waves reaching the tympanic membrane through natural means. In this regard, the in the ear device can be configured so as to "pass through" sound based on those bands and not the other bands. In an exemplary embodiment, this can be done without amplification. That is, the in the ear device can be configured to output a signal from projector 262 that is at the same amplitude or at least effectively the same amplitude as that which would result if the in the ear device was not present in the ear canal for those frequency bands, and not output any signal for the other frequency bands. That said, in some alternate embodiments, amplification can be applied to some or all of those frequency bands (the bands corresponding to the bands for acoustic hearing that provide more information than that which results from electric hearing.

Figure 11:
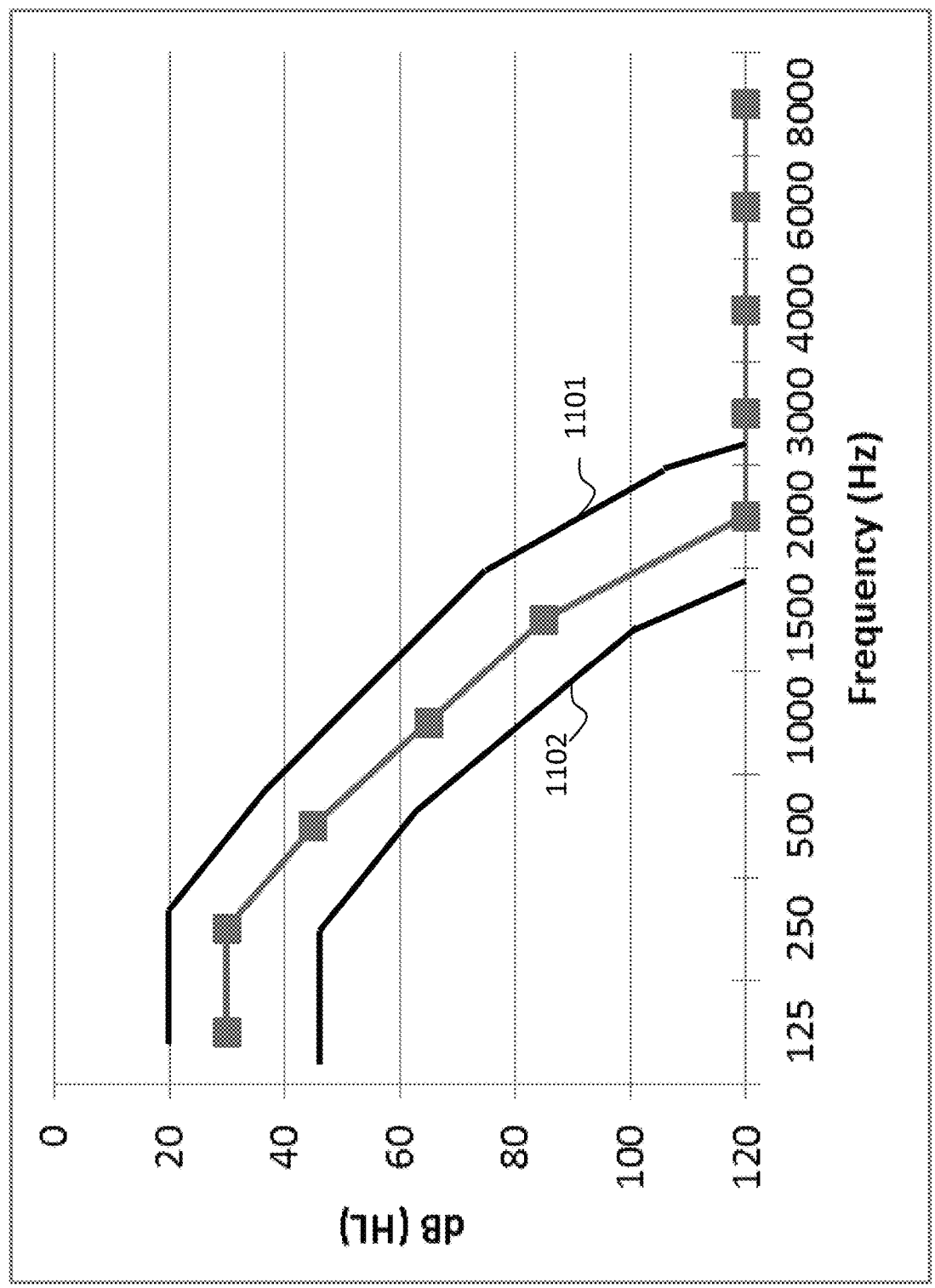
FIG. 11 presents another graph of exemplary data according to an exemplary embodiment.

It is briefly noted that in at least some exemplary embodiments, the data utilized to develop the functions of FIGS. 4 and/or 5 is data developed from electric hearing users that have residual hearing. In an exemplary embodiment, the normative data developed for these FIGs. is developed utilizing a statistically significant group having residual hearing concomitant with that of the recipient. By way of example only and not by way of limitation, the frequencies of the residual hearing for the members of the statistically significant group can correspond or otherwise generally correspond to those of the individual. In an exemplary embodiment, the deficiencies of the members of the statistically significant group with respect to residual hearing for those frequencies can correspond or otherwise generally correspond to those of the individual. By way of example only and not by way of limitation, the data associated with FIG. 6 can be data that is at least generally applicable to those members of the statistically significant group, where the data of FIG. 6 also corresponds to the individual for whom the prescription is being prepared. In this regard, FIG. 11 depicts an exemplary "tolerance range" bounding the data curve associated with FIG. 6. In an exemplary embodiment, with respect to executing method 300 or the other methods detailed herein for recipients for which the prescription of the methods detailed herein is prepared having residual hearing falling within tolerance curves 1101 and 1102, method action 310 could utilize a first data set when executing method 310 vis-à-vis the data for electric hearing, and for a recipient for which the prescription of the methods detailed herein is prepared having residual hearing falling outside tolerance curves 1101 and/or 1102, method action 310 could utilize a second data set and/or a third data set when executing method 310.

Thus, in an exemplary embodiment, the data utilized in method action 310 can be different for one recipient relative to another recipient. Note also that this difference is not always related to the residual hearing. Differences in the data utilized for one recipient relative to that of another recipient in method action numeral 310 could relate to the fact that different recipients respond to electric hearing differently. For example, recipients that receive cochlear implants in both middle ears may respond differently in a statistically significant manner as a class then recipients that receive cochlear implants in only one middle. Age groups can also be a basis to utilize different normative data for different individuals. Gender, native language, occupation (labor vs. office worker, etc.), habitat (city dweller vs. country folk), etc. can utilize a basis for utilizing different normative data in method action 310.

Figure 12:
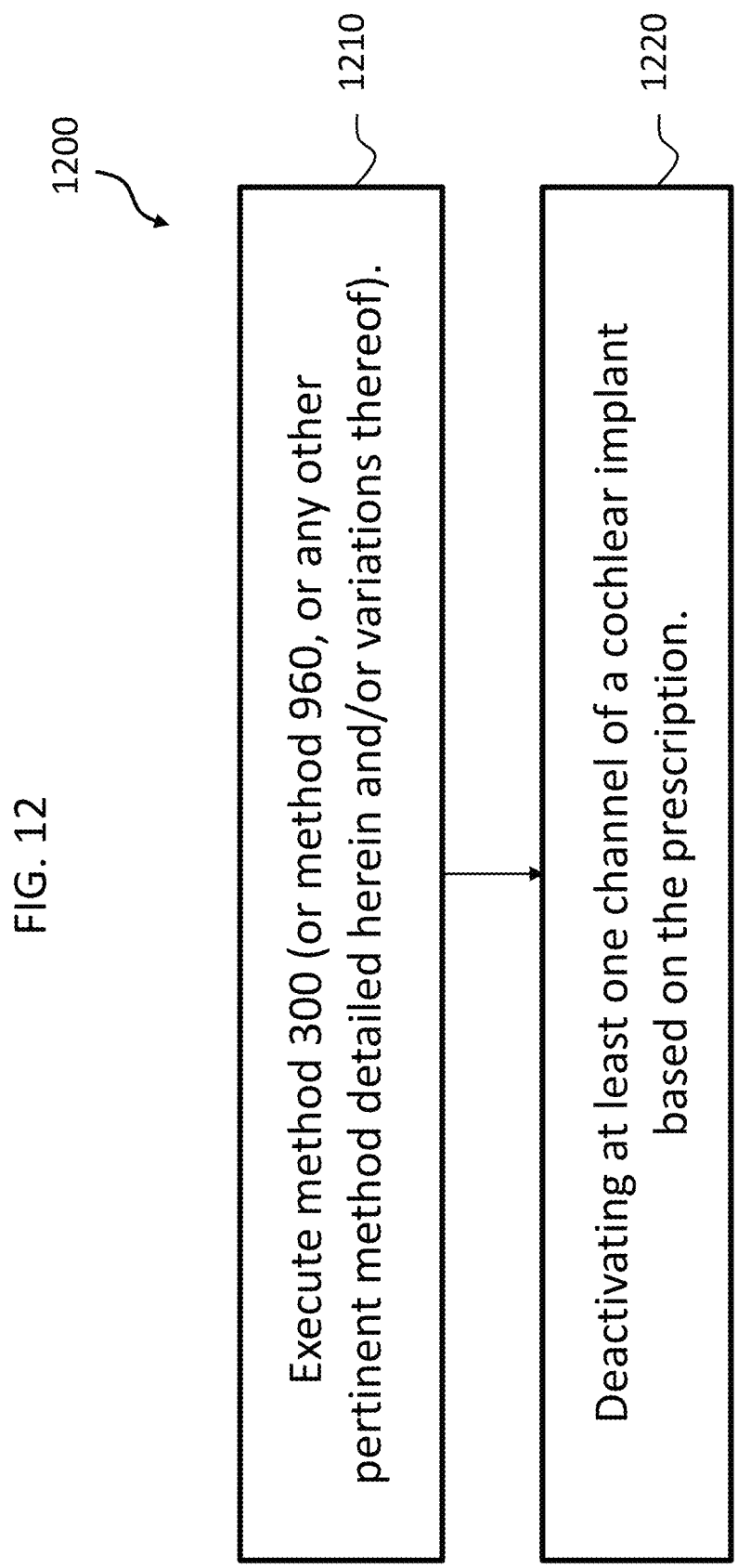
FIG. 12 presents another exemplary flowchart for an exemplary method according to an exemplary embodiment.

FIG. 12 presents another exemplary flowchart for another exemplary method according to an exemplary embodiment. The flow chart of FIG. 12 represents method 1200. Method 1200 includes method action 1210, which entails executing method 300, or any other methods detailed herein, such as method 960 or variations thereof. Method 1200 further includes method action 1220, which entails deactivating at least one channel of a cochlear implant based on the prescription. Briefly, it is noted that method action 1200 can alternatively entail not activating at least one channel of a cochlear implant while activating at least one other channel of the cochlear implant. That is, some embodiments of a cochlear implant can be such that the channels must be activated individually for those channels to be utilized. If no channel is activated, the cochlear implant will never work. Alternatively, some embodiments of the cochlear implant can be such that all channels are initially activated upon startup, and channels must be affirmatively deactivated to eliminate that channel or otherwise prevent that channel from being utilized as a basis to energize one or more the electrodes of the electrode array. It is noted that the term activated and deactivated as used herein corresponds to the setting or otherwise configuring the electrode array such that for a captured sound having a sound content across the entire audio spectrum, the activated channels will utilize as a basis to energize the electrode, and the deactivated channels will not utilize a basis to energize electrodes. This as distinguished from a scenario where a captured sound has a narrow frequency range, and thus a cochlear implant with all channels enabled only energizes a subset of the electrodes corresponding to the frequency range that captured sound (how a cochlear implant normally works with all channels enabled). That is, "activation" does not simply mean what happens when a channel is utilized as a basis to evoke a hearing percept simply because sound content has a frequency corresponding that channel.

Thus, it is to be understood that in an exemplary embodiment, the prescription can be utilized by an audiologist or the like at the time of fitting or even at the time of implantation where before implantation prior to fitting, or post implantation prior to fitting, to deactivate or otherwise set the cochlear implant so that certain channels thereof are not utilized as a basis to evoke a hearing percept utilizing electrical hearing. In an exemplary embodiment, this can entail programming the sound processor of the hearing prosthesis to not utilize those channels as a basis to provide energizement to the electrode array. In an exemplary embodiment, this can entail programming the sound processor the hearing prosthesis to only utilize other channels as a basis to provide energizement to the electrode array. In an exemplary embodiment, this can entail physically altering the prosthesis (e.g., filter banks can be included or removed). In an exemplary embodiment, this can entail adjusting a bandpass filter that only passes a signal having a frequency above a certain level (or at and above a certain level) to the sound processor (or adjusting a filter that is part of the sound processor). In an exemplary embodiment, this can entail removing filters from the hearing prosthesis. Any device, system, and/or method that can be utilized to activate and/or deactivate channels of a hearing prosthesis can be utilized in at least some exemplary embodiments.

Figure 13:
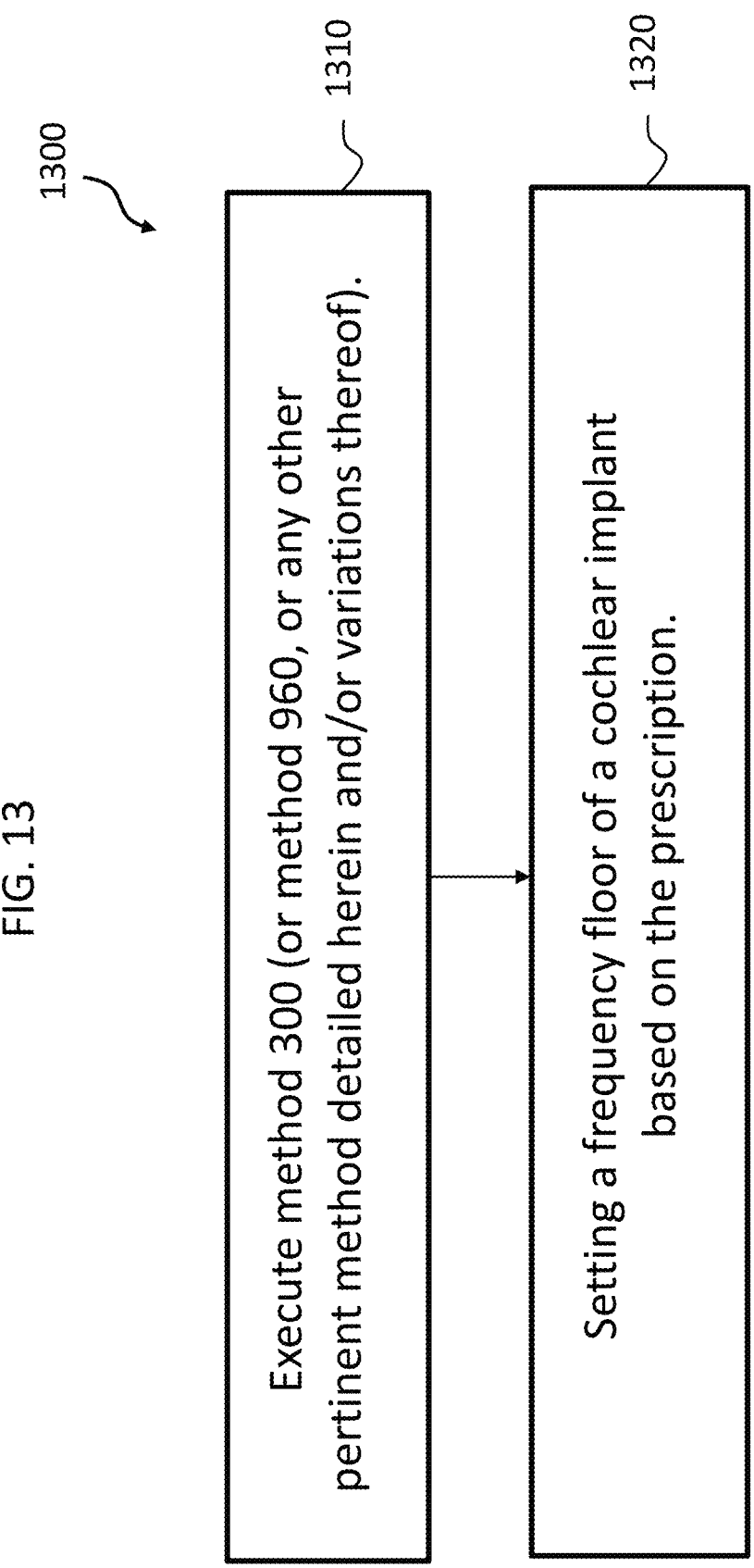
FIG. 13 presents another exemplary flowchart for an exemplary method according to an exemplary embodiment.

Thus, now referring to FIG. 13, which presents an exemplary flowchart for an exemplary method 1300 which includes method actions 1310 and 1320. Method action 1310 corresponds to method action 1210 detailed above. Method action 1320 entails setting a frequency floor of a cochlear implant based on the prescription developed by executing method action 1310. In this regard, this can entail adjusting or otherwise setting or otherwise activating or deactivating given channels so that the cochlear implant will not provide stimulation to the recipient below a certain frequency (the floor) regardless of the frequency content of the captured sound or otherwise the ambient sound. It is noted that the claim phrase "frequency floor" entails both an embodiment where the cochlear implant does not provide stimulation based on frequencies at values below the frequency corresponding to the floor (but does provide stimulation at frequencies corresponding to the value of the floor), as well as in some alternative embodiments an embodiment where the cochlear implant does not provide stimulation based on frequencies below the frequency corresponding to the floor and does not provide stimulation based on frequencies corresponding to the floor.

Figure 14:
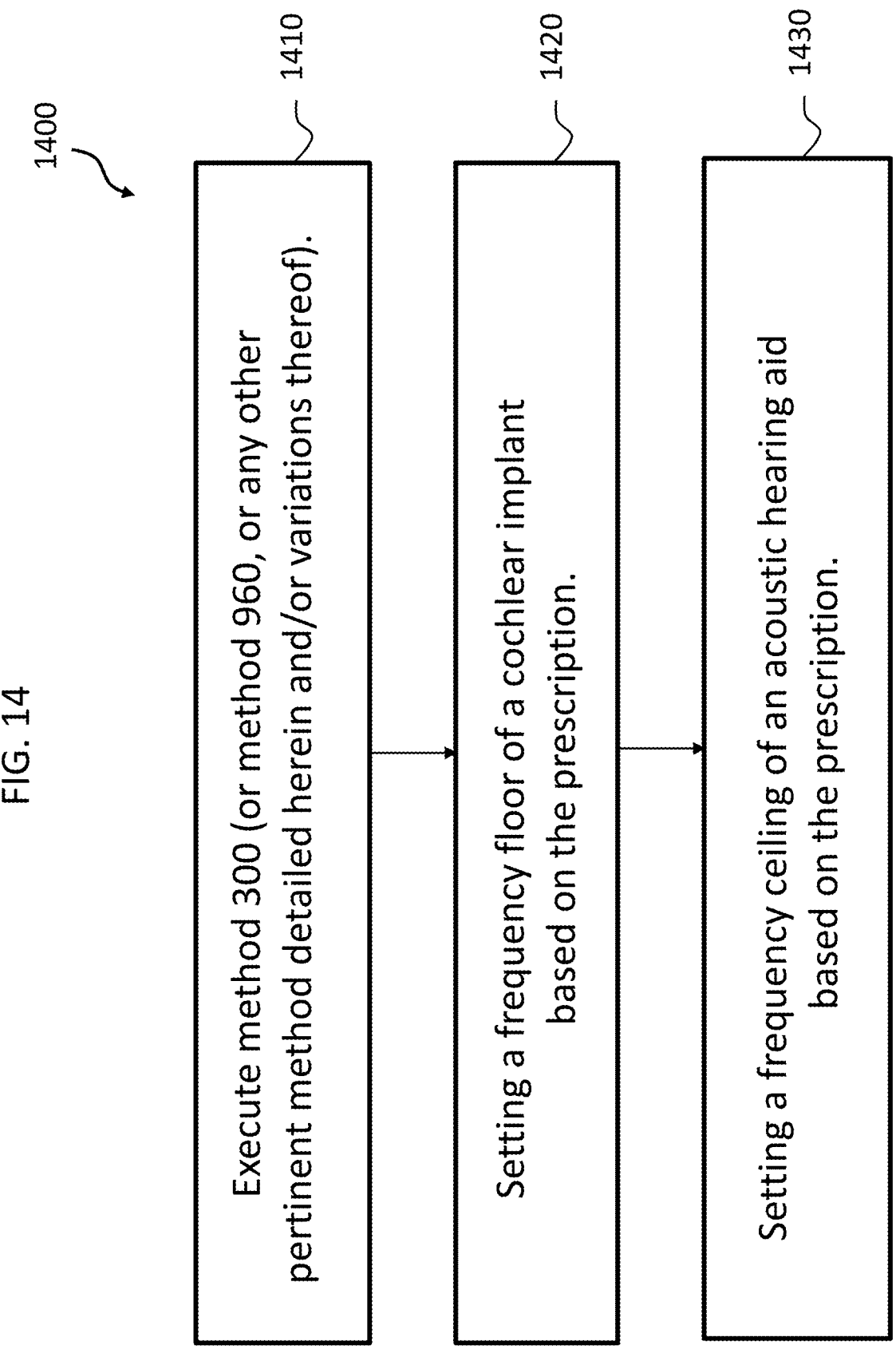
FIG. 14 presents another exemplary flowchart for an exemplary method according to an exemplary embodiment.

Briefly, the embodiments of FIGS. 12 and 13 have been directed towards scenarios where the prosthesis can be a multimodal prosthesis or a unimodal prosthesis. That is, by way of example only and not by way of limitation, there may or may not be a conventional acoustic hearing aid that is part of the hearing prostheses. That said, some embodiments of the teachings detailed herein are directed towards preparing a prescription for a multimodal prosthesis. Accordingly, FIG. 14 depicts an exemplary flowchart for an exemplary method 1400. Method 1400 includes method action 1410, which entails executing method action 1210 detailed above. Method 1400 further includes method action 1420, which corresponds to method action 1320 detailed above. Method 1400 further includes method action 1430 which entails setting a frequency ceiling of an acoustic hearing aid based on the prescription developed in method action 1410. Method action 1420 can entail adjusting or otherwise setting or otherwise activating or deactivating given channels so that the acoustic hearing aid will not provide stimulation to the recipient above a certain frequency (the ceiling) regardless of the frequency content of the captured sound or otherwise the ambient sound. It is noted that the claim phrase "frequency ceiling" entails both an embodiment where the acoustic hearing aid does not provide stimulation at frequencies corresponding to frequencies above the value corresponding to the floor (but does provide stimulation at the frequency corresponding to the floor), as well as embodiments where the acoustic hearing aid does not provide stimulation at frequencies corresponding to frequencies above the value corresponding to the floor as well as frequencies corresponding to the floor.

It is briefly noted that the actions of setting the ceilings and/or floors and/or activating and/or deactivating channels and/or adjusting the implants is executed prior to the implementation of any meaningful fitting actions, at least in some exemplary embodiments. In this regard, in an exemplary embodiment, a fitting procedure can begin where one of the first actions is to set the hearing prosthesis according to the prescription. Indeed, the first action associated with adjusting the prosthesis can entail setting or otherwise adjusting the prosthesis according to the prescription. With the hearing prosthesis set according to the prescription, the hearing prosthesis is then proceeded to be fitted to the recipient.

It is also noted that in some alternate embodiments, full frequency ranges are set based on the prescription. By setting a full frequency range or even a partial frequency range, by definition, frequency ceilings and frequency floors are set, those corresponding to the highest and lowest frequencies of those ranges. Thus, any action of setting or otherwise establishing or otherwise adjusting a frequency range of a cochlear implant corresponds to the setting of a frequency ceiling a frequency floor of the prosthesis.

Indeed, in an exemplary embodiment, one or more of the method actions detailed herein and/or variations thereof are executed prior to obtaining comfort and/or threshold levels of the recipient with respect to the cochlear implant it implanted in the recipient. By way of example only and not by way of limitation, the prescription can be prescribed and/or the prosthesis can be set based on that prescription prior to an audiologist or the like testing the current levels to evoke a threshold response and/or the current levels that corresponds to the comfort level of the recipient (T and C levels). By way of example only and not by way of limitation, the prescription can be prescribed and/or the prosthesis can be set based on that prescription prior to an audiologist or the like developing an audiogram for electric hearing for that recipient. That said, in some exemplary embodiments, the prescription can be prescribed and/or the prosthesis can be set based on that prescription at the beginning of the fitting process.

In an exemplary embodiment, the prescription developed according to the teachings entailed herein is limited to only the frequencies to allocate to acoustic hearing and those to allocate to electric hearing. In an exemplary embodiment, the prosthesis is set according to the prescription during the fitting process, but prior to the following actions, and/or subsequent to the development of the prescription, both the electric hearing device and acoustic hearing device (if present) are configured for use. Subsequent to the development of the prescription, the electric hearing device component is configured with the recipient listening to signals generated by the programming system (280 in FIG. 1). This involves setting the T and C levels on the electrodes to be used, as described herein. The acoustic hearing device, if present, is also configured subsequent to the development of the prescription, but can be configured prior to the fitting process.

Prior to fitting, but after the development of the prescription developed herein, the acoustic hearing device, if present, can be configured so that the gain (amplification) settings (prescription) are appropriately adjusted on the frequency channels to be used. This would be based on one of the several hearing aid prescriptions.

Once the acoustic hearing device, if present, is configured, it is then fit to the recipient in the fitting session. In at least some embodiments, because the individual is unique, with respect to the acoustic characteristics of the ear canal, it is utilitarian to ensure that the frequency gains set in the device are actually delivered. There are several standard tests that measure the delivered gain. Common ones are Real Ear Insertion Gain (REIG) or Real Ear Aided Gain (REAG). These are all executed, in some embodiments, after development of the prescription according to the teachings detailed herein.

It is noted that in some embodiments, because a sub-set of frequencies is used, as opposed to a full set of frequencies, modification of a standard hearing aid prescription (gain settings) might be utilitarian. A modification of the gain settings can be used that is a deviation from the standard gain prescriptions. One modification could be a prescribed adjustment of gain (increase or decrease) so that the acoustic loudness better matches that from electric hearing.

Another action executed after the above, including after development of the prescription, is that actions are taken to ensure or otherwise drive the overall loudness of sounds to be comfortably loud and do not produce discomfort. This involves presenting acoustic sounds to the recipient, such as talking to the person, but can also be signals presented via a loudspeaker, at appropriate dB levels, to the recipient, and ensuring or otherwise verifying that the loudness percept is comfortably loud and does not produce discomfort. If the percept is not appropriate, either the acoustic or electric component, or both, would be adjusted based on the subjective feedback. For the acoustic hearing device, this would be the gain settings, while for the electric hearing device, this would be the T and/or C levels.

Of course, it is noted that when using natural hearing there is no adjustment of the acoustic device because it is not used.

Figure 15:
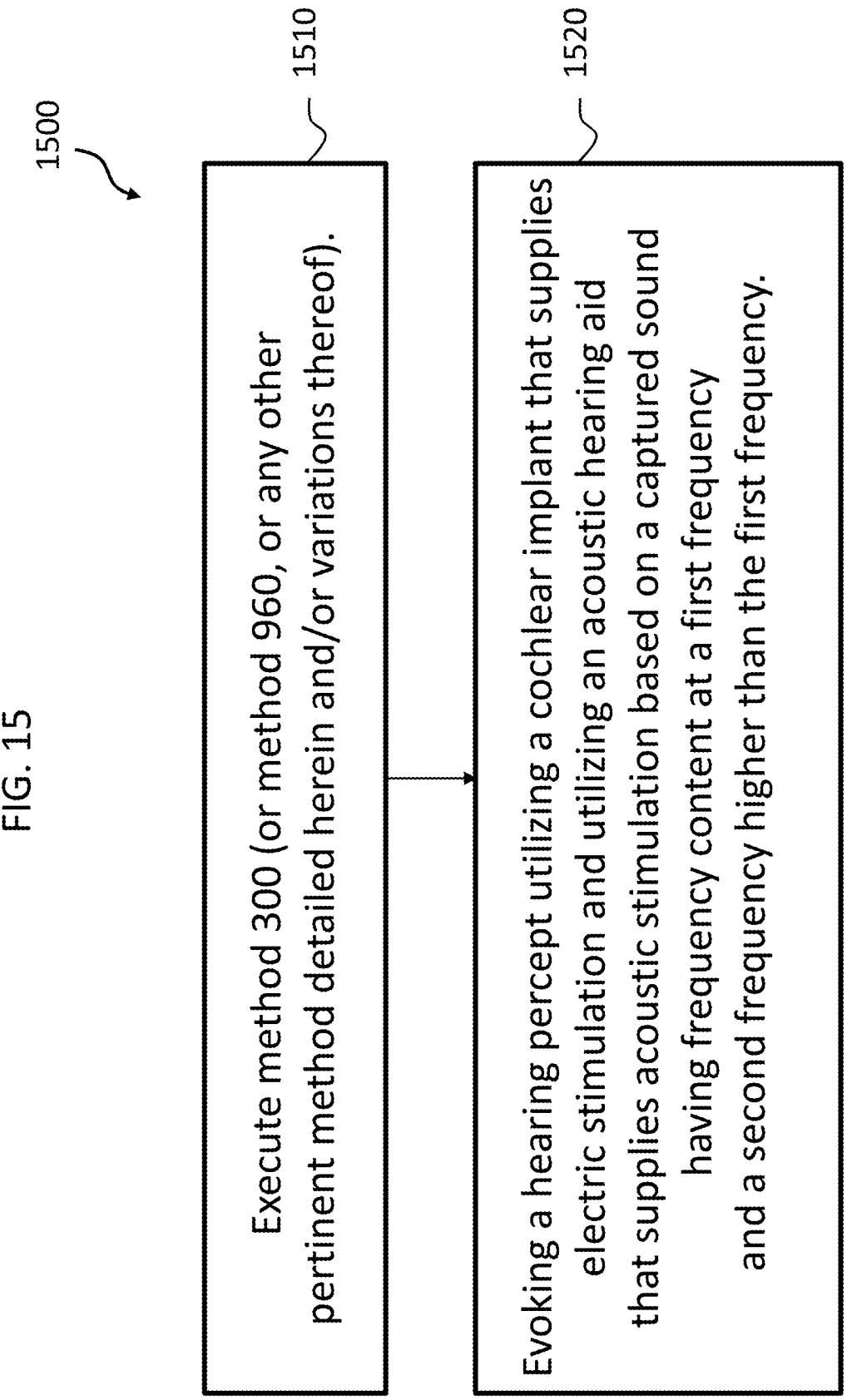
FIG. 15 presents another exemplary flowchart for an exemplary method according to an exemplary embodiment.

FIG. 15 presents an exemplary flowchart for an exemplary method 1500. Method 1500 includes method action 1510, which corresponds to method action 1210 detailed above. Method 1500 further includes method action 1520, which entails evoking a hearing percept utilizing a cochlear implant that supplies electric stimulation and utilizing an acoustic hearing aid that supplies acoustic stimulation based on a captured sound having frequency content at a first frequency (e.g., 400 Hz) and a second frequency (e.g., 3,000 Hz) higher than the first frequency. In an exemplary embodiment, the electric stimulation can be based on the second frequency but not the first frequency. Still further, in an exemplary embodiment, the acoustic stimulation can be based on the first frequency but not the second frequency. Still further, in this exemplary embodiment, the bifurcation between the second frequency and the first frequency is based on the prescription obtained or otherwise developed per method action 1510. It is noted that in the aforementioned exemplary embodiment, the first frequency content can be a range (e.g., a range no greater than about 100, 150, 200, 250, 300, 350, 400, 450, 500, 550, 600, 650, 700, 750, 800, 850, 900, 950, or 1,000 Hz) and the second frequency content can also be a range. It is also noted that the frequency contents can correspond to relative major content with respect to a captured sound. In this regard, a captured sound can have frequency content from, for example, 150 Hz to 4,500 Hz, where there are two maxima at two different frequency ranges (e.g., a maxima at frequency range between 300 Hz-600 Hz and 3,000 Hz-3,500 Hz), those ranges corresponding to the first and second frequency content of the aforementioned method action 1520. It is noted that there can be more than two maxima at more than two different frequency ranges (e.g., an additional maxima at a range between 700-750 Hz and/or an additional maxima at a range between 4,500 and 4730 Hz, etc.). Any of these maxima can correspond to frequency content.

In view of the above, it is to be understood that in an exemplary embodiment, there is a method of setting a cochlear implant to operate based on data based on a comparison of first data for electric stimulation to evoke a hearing percept with second data for a second type of stimulation to evoke a hearing percept different from the electric stimulation. In an exemplary embodiment, the first data corresponds to any of the data detailed above and/or variations thereof, such as by way of example only and not by way of limitation, data relating to FIG. 4 and five. In an exemplary embodiment, the second data can correspond to any of the data detailed above and/or variations thereof such as by way of example only and not by of way limitation, data relating to FIGS. 7 and 8, which, as noted above, is for acoustic hearing. In some embodiments, the second type of stimulation can be natural and unamplified acoustic stimulation. In some embodiments, the second type of stimulation can be amplified acoustic stimulation, such as that which results from utilization of the in the ear device 250, while in some embodiments, the second type of stimulation can be non-amplified while still resulting from the in the ear device 250. That said, in some embodiments, the second type of stimulation can correspond to that which results from the utilization of a middle ear implant. Indeed, in some exemplary embodiments, the recipient previously utilized a middle ear implant for all hearing through all frequencies, but due to deterioration of the inner ear, the middle ear implant became less effective, including ineffective at the higher frequencies. Still further, in some embodiments, the second type of stimulation can correspond to that which results from the utilization of a bone conduction device, where again, the recipient could have previously utilized a bone conduction device for all hearing through all frequencies.

Consistent with the teachings detailed above, in an exemplary embodiment, the first data can be data based on a cumulative contribution for electric stimulation. As noted above, in an exemplary embodiment, the first data can be normative data based on a statistically significant group. Also consistent with the teachings detailed above, in an exemplary embodiment, the second data can be data based on a cumulative contribution for the second type of hearing stimulation. In an exemplary embodiment, this can be normative data and/or can be subjective data related to or otherwise based on the individual receiving the cochlear implant. With respect to the phrase "cumulative contribution," it is meant that the data was developed by progressively eliminating frequency bands and maintaining the elimination of the frequency bands as detailed above. This is as opposed to an embodiment where the hearing tests are applied such that a given frequency band is eliminated, and then another frequency band is eliminated but the previous frequency band that was eliminated is no longer eliminated.

Thus, consistent with the teachings detailed above, in an exemplary embodiment, the data for electric stimulation is relative cumulative contribution data for relative frequency bands of ascending frequency. Still further, consistent with the teachings detailed above, in an exemplary embodiment, the data for the second type of hearing stimulation is relative cumulative contribution data for respective frequency bands of descending frequency.

Figure 16:
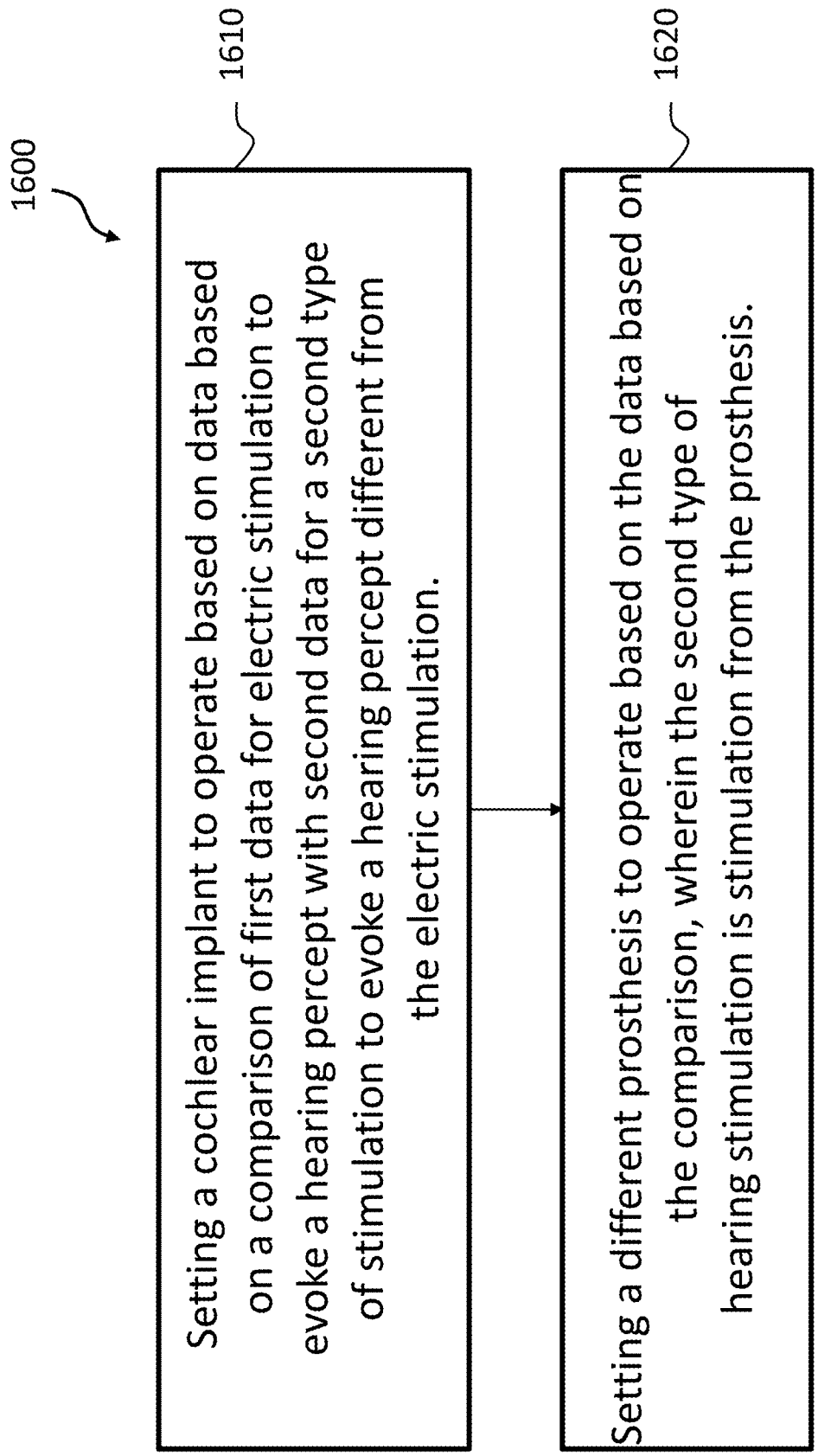
FIG. 16 presents another exemplary flowchart for an exemplary method according to an exemplary embodiment.

Thus, FIG. 16 presents an exemplary flowchart for an exemplary method 1600, which includes method 1610, which includes setting the cochlear implant to operate as noted above based on the aforementioned noted comparison. Method 1600 further includes method action 1620, which entails setting a different prosthesis (different from the cochlear implant sat in method action 1610) to operate based on the data based on the comparison of method action numeral 1610, wherein the second type of hearing stimulation is stimulation from the prostheses. In this regard, in an exemplary embodiment, the prostheses of method action 1620 can be an acoustic hearing aid, wherein the second type of hearing stimulation is acoustic stimulation. That said, in an exemplary embodiment, as would be understood from the above, there is no method action 1620. Such an exemplary method can result from the utilization of a unimodal prosthesis. For example, method action 1620 can be executed in a manner solely directed to the cochlear implant, because the recipient does not utilize an acoustic hearing aid.

Still further, in an exemplary embodiment, method action 1620 entails setting a middle ear prosthesis to operate based on the data based on the comparison executed in method action 1610, wherein the second type of hearing stimulation is hearing stimulation from the middle ear implant. Also, in an exemplary embodiment, method action 1620 entails setting a bone conduction device to operate based on the data based on the comparison executed in method action 1620, wherein the second type of hearing stimulation is hearing stimulation from the bone conduction device.

In an exemplary embodiment, method action 1610 is such that the action of setting the cochlear implant maximizes the second type of stimulation at frequency bands where the electric stimulation provides inferior speech perception relative to the second type of stimulation, and maximizes the second type of stimulation at no other frequency bands. In this regard, as noted above, frequency bands for the second type of stimulation, such as acoustic stimulation, are maximized only where it matters or otherwise only where such results in a utilitarian results beyond that which would be the case if those frequency bands were instead applied to the cochlear implant.

Still, referring to the embodiments that utilize a multimodal prosthesis, in an exemplary embodiment, the cochlear implant is part of a multimodal hearing prosthesis (a multimodal prosthesis) that evokes an electric hearing percept at some frequencies and not other frequencies (e.g., because some channels have been deactivated or otherwise disabled, etc.). In an exemplary embodiment, the cochlear implant would be fully capable of evoking hearing percepts at the other frequencies if such was permitted (e.g., the bands were not disabled or otherwise deactivated). To this end, the cochlear implant has respective channels for respective sound frequency bands, and the action of setting the cochlear implant maximizes speech understanding in hearing percepts resulting from the second type of stimulation for frequencies that provide less contribution to speech understanding for the electric stimulation than the second type of stimulation. Still further, in some exemplary embodiments, the comparison of method action 1610 is such that the comparison indicates that for a first frequency band from the plurality of frequency bands and for frequency bands below that first frequency band, cumulative contribution for the second type of hearing stimulation is greater than the cumulative contribution for the electric stimulation, and the action of setting the cochlear implant entails at least one of deactivating channels or not activating corresponding to frequency bands at and below the first frequency band.

Figure 17:
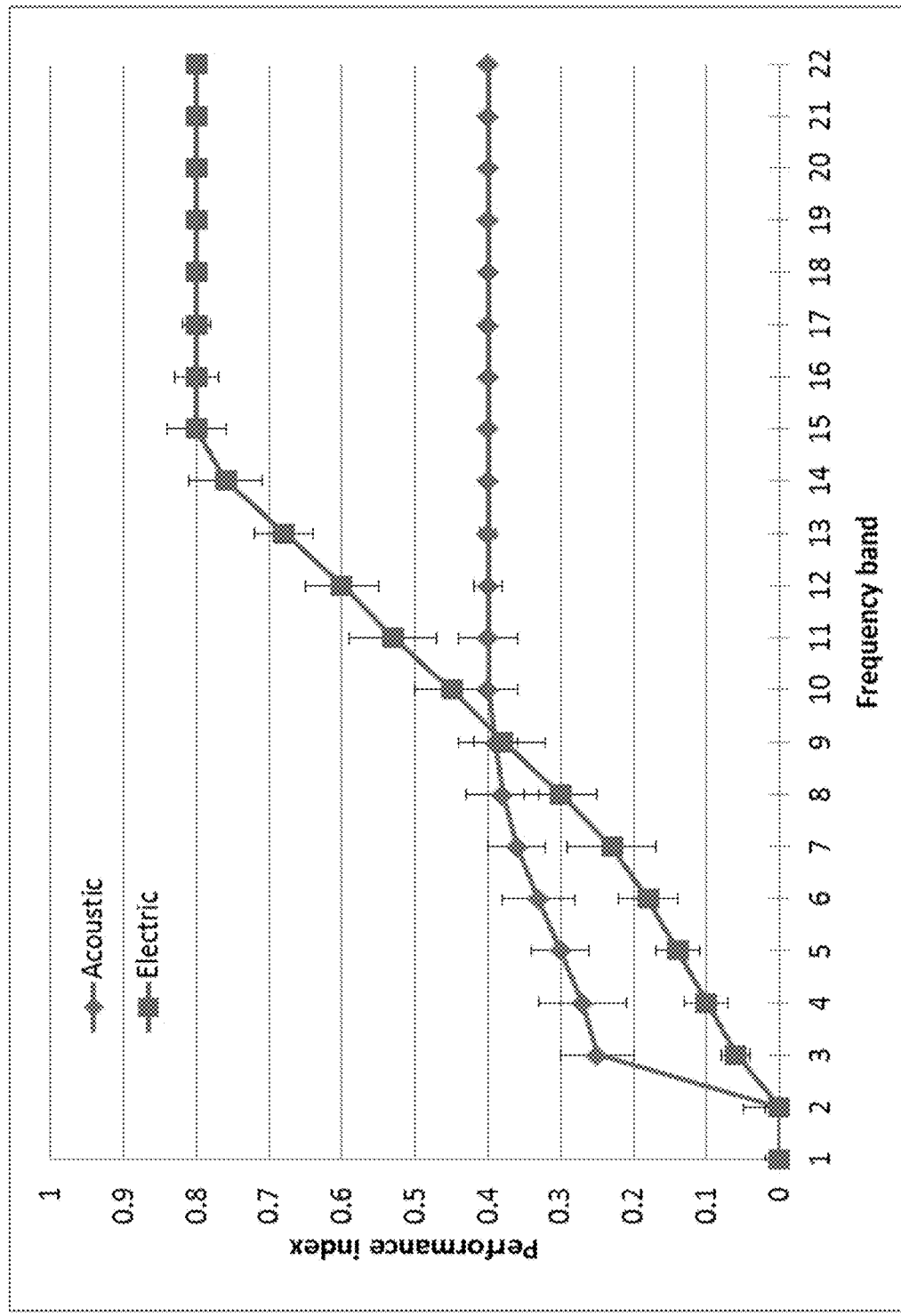
FIG. 17 presents another graph of exemplary data according to an exemplary embodiment.

It is noted that the aforementioned crossover frequency (exact frequency or frequency band) can be established utilizing probability theory and/or likelihood theory. For example, the normative data for electric and acoustic stimulation can, in at least some exemplary embodiments, include measures of between-subject variation. For example, standard deviation, 25% and 75% quartiles, or other similar measures of confidence intervals, can be utilized. FIG. 17 presents the detail of FIG. 10 (cumulative contributions of frequency bands for electric and acoustic stimulation with confidence intervals), but with confidence intervals for each data point. The confidence intervals can be incorporated into equation (11) using:

$$\text{IF } EB(SL_e, ECF_l)_{1 \to n} > AB(SL_a, ACF_u)_{22 \to n} \text{ THEN} \\ CF = n \quad (12)$$

Where $ECF_l$ is the lower bound of the electric confidence interval and $ACF_u$ is the upper bound of the acoustic confidence interval.

In an exemplary embodiment, the various method actions detailed herein and/or variations thereof associated with comparing the data associated with electric hearing to that of the acoustic hearing can take into account the confidence intervals associated with the data. In an exemplary embodiment, the comparison can be executed utilizing weighting factors that address the confidence intervals. By way of example only and not by way of limitation, with respect to FIG. 17, an exemplary embodiment can entail selecting frequency band 10 as the last frequency band for acoustic hearing because the probability interval encompasses the curve of the electric hearing at that frequency band, even though the curve for electric hearing is higher than the curve for acoustic hearing. That said, in an alternative embodiment, the frequency band 7 could be selected as the last frequency band for acoustic hearing because that is the last band where the confidence intervals do not overlap. In a similar vein, frequency band 10 could be selected as the last frequency band for acoustic hearing because the confidence intervals overlap, irrespective of the fact that the confidence interval for acoustic hearing overlaps the actual curve of the electric hearing. Corollary to this is that in an exemplary embodiment, the default could be to electrical hearing when the confidence interval associated with the electrical hearing overlaps the confidence interval and/or curve of the acoustic hearing. Any regime of utilizing the confidence intervals can be utilized in at least some exemplary embodiments.

Figure 18:
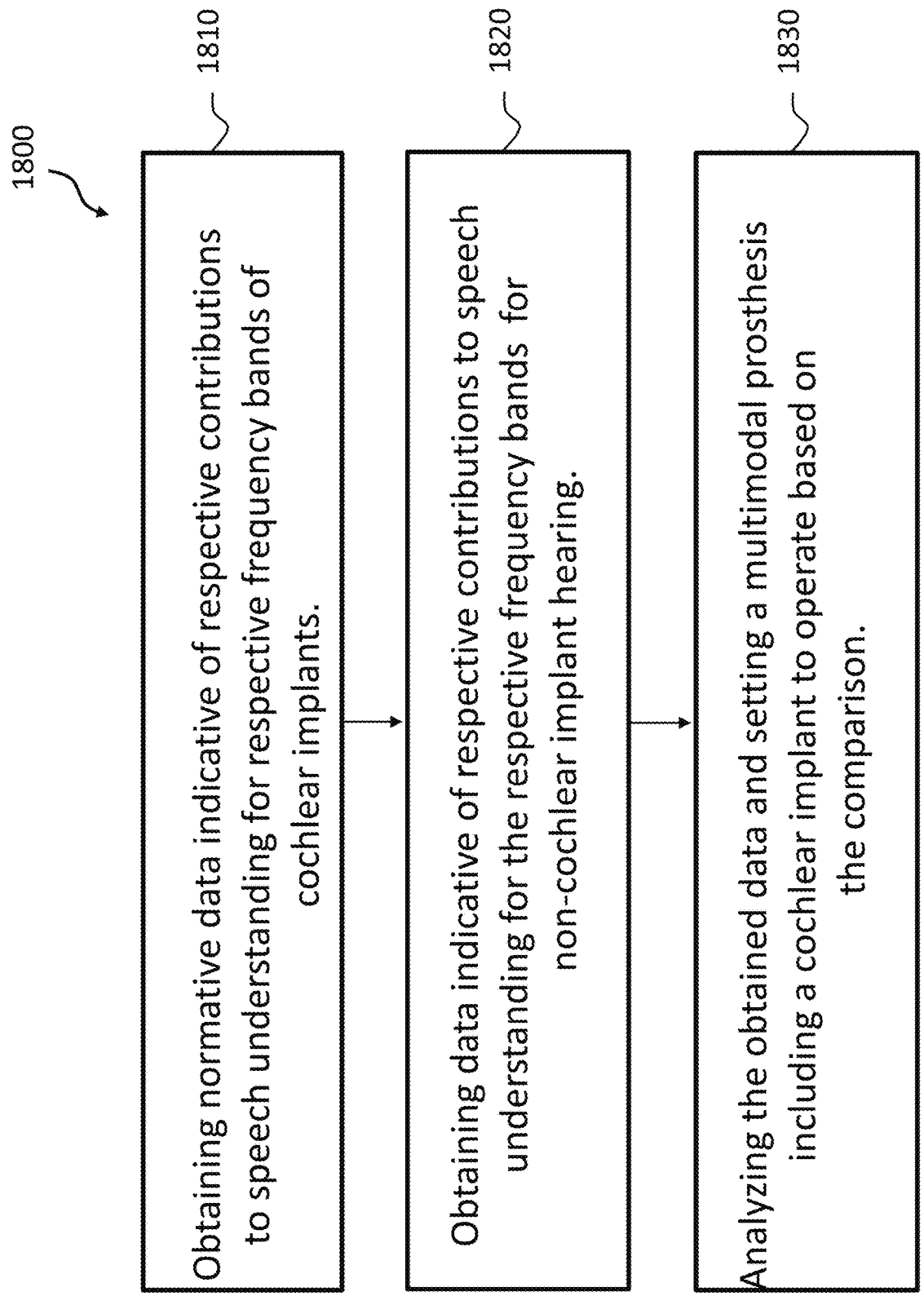
FIG. 18 presents another exemplary flowchart for an exemplary method according to an exemplary embodiment.

FIG. 18 presents an exemplary flowchart for an exemplary method 1800 according to an exemplary embodiment. Method 1800 includes method action 1810, which entails obtaining normative data indicative of respective contributions to speech understanding for respective frequency bands of cochlear implants. This can be executed according to the teachings detailed above. It is noted by the word "obtaining," this can entail actually conducting the hearing tests to develop the normative data, as well as simply obtaining the end results of such data. Method 1800 further includes method action 1820, which entails obtaining data indicative of respective contributions to speech understanding for the respective frequency bands for non-cochlear implant hearing. In an exemplary embodiment, this can be executed utilizing normative data as detailed above, alternatively and/or in addition to this, this can be executed utilizing individual data associated with the individual recipient. The non-cochlear implant hearing can be that of normal hearing without an acoustic hearing aid, hearing resulting from a middle ear implant, and/or hearing resulting from bone conduction techniques, etc. The non-cochlear implant hearing can be any type of hearing that can enable the teachings detailed herein and/or variations thereof.

Method 1800 further includes method action 1830, which entails analyzing the obtained data and setting a multimodal prosthesis according to a cochlear implant to operate based on the comparison. Such can entail adjusting the single sound processor of a multimodal prosthesis according to the teachings detailed herein, such that the sound processor utilizes certain frequency bands to evoke a hearing percept utilizing electrical hearing, and such that the sound processor utilizes other frequency bands to activate the ITE device or other device such that the projector 262 projects utilizing the other frequency bands. It is also noted that in some exemplary embodiments, the action of setting the multimodal prosthesis can be such that the acoustic portion or other non-cochlear implant portion of the multimodal prosthesis operates to output a signal at frequencies above the cutoff frequency, but those frequencies above the cutoff frequency are not amplified, whereas the frequencies that and/or below the cutoff frequency are amplified. In an exemplary embodiment, such can have utilitarian value with respect to replicating the real world situation that results from a given sound vis-à-vis the force applied to the tympanic membrane and/or the pertinent portions of the cochlea. That is, in some exemplary embodiments there can be utilitarian value with respect to implementing the teachings detailed herein where the non-cochlear implant prostheses, such as the in the ear (ITE) acoustic hearing aid, is configured such that the real-world the facts are not interfered with by that prostheses. For example, the in the ear (ITE) device could dampen or otherwise muffle the sound waves that impact on the tympanic membrane. Thus, the prosthesis could be set so as to amplify some frequencies, while also mimicking the natural impact on the tympanic membrane for the frequencies that are not amplified. That said, in some alternate embodiments, above the cutoff frequency, there is no activation of the non-cochlear implant prosthesis.

In an exemplary embodiment, the action of analyzing the obtained data in method action 1830 includes comparing the data for at least one of the respective frequency bands of cochlear implants to data for the corresponding frequency band for non-cochlear implant hearing to determine which contributes more to speech understanding, concomitant with the teachings detailed above. Still further, also concomitant with the teachings detailed above, the data for cochlear implants obtained in method action 1810 comprises data developed by progressively eliminating respective channels for cochlear implants implanted in a recipient and determining contributions to speech understanding for the cumulative channels that were eliminated. In this exemplary embodiment, the respective channels corresponding to the frequency bands of method action 1810. Again, the action of obtaining the normative data can entail obtaining the data without executing the actual hearing tests to develop the data. As long as that data is based on data developed by progressively eliminating the respective channels as just noted, such meets the method action 1810 as further specified.

Corollary to this is that in an exemplary embodiment, the data for non-cochlear implant hearing comprises data developed by progressively eliminating frequency bands in descending order from sound exposed to an individual and/or a plurality of individuals. In an exemplary embodiment, the individual is the recipient of a multimodal prosthesis that is set method action 1830. Conversely, as will be understood from the above, in an exemplary embodiment, the plurality of individuals constitutes the statistically significant group that was utilized to develop the normative data for the acoustic hearing or the non-cochlear implant hearing. In an exemplary embodiment, based on the data developed by the progressive elimination of frequency bands, contributions to speech understanding for the cumulative frequency bands eliminated is determined. Such can be practiced according to the teachings detailed above.

Also consistent with the teachings detailed above, in an exemplary embodiment, the action of setting the multimodal prosthesis in method action 1830 entails at least one of disabling channels where not activating channels of the cochlear implant corresponding to frequency bands for non-cochlear implant hearing that cumulatively contribute more to speech understanding then the disabled channels of the cochlear implant on a cumulative basis. With respect to the data associated with FIG. 17, this could entail disabling and/or not activating channels 1 to 7 of the cochlear implant, 1 to 8 of the cochlear implant, or 1 to 9 of the cochlear implant, or channels 1 to 10 of the cochlear implant, depending on whether or not the probability theory is implemented and how that probability theory is implemented. Moreover, in an exemplary embodiment, the data for non-cochlear implant hearing comprises data developed by progressively eliminating frequency bands from sound exposed to an individual corresponding to the recipient of the multimodal prosthesis and determining contributions to speech understanding for the cumulative frequency bands eliminated. In an exemplary embodiment, the data for non-cochlear implant hearing developed with respect to the individual is obtained prior to implantation of the cochlear implant into the recipient. That said, in an alternate embodiment, the data for non-cochlear implant hearing developed with respect to the individual is obtained after implantation of the cochlear implant into the recipient.

It is also noted that in an exemplary embodiment, the hearing test can be applied to the individual before and/or after implantation of the hearing prosthesis, and the non-cochlear implant hearing data can be developed accordingly. An exemplary method entails comparing that data for the individual to the normative data for the non-cochlear implant hearing, and determining that the individual data where the normative data has more utilitarian value with respect to implementing the teachings detailed herein and/or variations thereof, based on some standard, and selecting the data that has more utilitarian value to implement the teachings detailed herein. In an exemplary embodiment, statistical techniques can be utilized to analyze the data based on the individual and determine whether or not that data is likely to have utilitarian value beyond that which would result from utilizing the normative data for that type of non-cochlear implant hearing. Also consistent with the teachings detailed above, in some embodiments, the data for non-cochlear implant hearing comprises data developed by progressively eliminating frequency bands from sound exposed to a statistically signification group of individuals and determining contributions to speech understanding for the cumulative frequency bands eliminated. Here, in an exemplary embodiment, data for non-cochlear implant hearing is obtained prior to implantation of the cochlear implant into the recipient.

As detailed above, the contribution from consecutive frequency bands are used. The order of band removal to measure a band's contribution is low-to-high for electric stimulation and high-to-low for acoustic stimulation. For acoustic stimulation, the SII variables can also be applied (but other variables can be applied). For electric stimulation, the variables can be the same or different, but are likely to be similar but have a different weight.

As noted above, many of the actions detailed herein are related to pre-fitting actions. Accordingly, in an exemplary embodiment, method 1600 in total or at least method action 1610 is executed prior to the commencement of any fitting method of the hearing prostheses. That said, in some alternate embodiments, method action 1600 or components thereof are part of a fitting process. In this regard, the action of setting the cochlear implant can be executed during a fitting session of fitting the cochlear implant to the recipient. With respect to the cochlear implant that has respective channels for respective sound frequency bands, the action of setting the cochlear implant maximizes acoustic hearing for sound falling within a first subset of the sound frequency bands and does not maximize acoustic hearing for sound falling within a second subset of the sound frequency bands immediately adjacent to the first subset. Still further, the acoustic hearing cannot maximize information beyond that of the cochlear implant for sound falling within the second subset. That is, irrespective of the amplification or the like of the acoustic content of all or part of the second subset, the electric hearing will maximize the information beyond that of the acoustic hearing if applied, even for a part of the subset. In this regard, in an exemplary embodiment, the setting of the cochlear implant to stimulate at frequencies higher than that which would result from implementing the teachings detailed herein and not at the frequencies that would result from implementing the teachings detailed herein would result in less speech understanding than that which would be the case if the cochlear implant was set to stimulate at the frequencies resulting from implementation of the teachings detailed herein, all other things being equal. Corollary to this is that in an exemplary embodiment, the setting of the acoustic implants or other non-electric implant to stimulate at frequencies higher than that which would result from implementation of the teachings detailed herein and not only at the frequencies that would result from implementation of the teachings detailed herein would result in less speech understanding than that which would be the case if the nonelectric implant was set to stimulate at the frequencies resulting from implementation of the teachings detailed herein, all other things being equal.

It is noted that the teachings detailed herein can be utilized in conjunction with fine-tuning operations of a fitting method. In some exemplary embodiments, the fine-tuning operations of a fitting method can result in a change to the settings of the hearing prosthesis from that of the prescription. By way of example only and not by way of limitation, the implementation detailed above are such that there is no overlap and/or additional separation in band allocation between the electric hearing bands and those of the non-electric hearing bands. Overlap of bands, where one or more bands are allocated to both acoustic channels and electrodes, or additional band separation, where one or more bands are completely removed, is part of the fine-tuning process to meet individual needs and is not included in the prescription description. Thus, an exemplary embodiment can entail setting the prosthesis to utilize electric hearing for a first subset of bands according to the prescription, and then adjusting or otherwise resetting the prosthesis to utilize electric hearing for a different subset of bands and/or over a greater range or a more limited range of bands than that which is prescribed, where this latter adjustment/resetting is executed based on the fine-tuning operations of the fitting method. Still further, an exemplary embodiment can entail setting the prosthesis to utilize acoustic hearing for a second subset of bands according to the prescription, and then adjusting or otherwise resetting the prosthesis to utilize acoustic hearing for a different subset of bands and/or over a greater range or a more limited range of bands than that which is prescribed.

In an exemplary embodiment, the prescription will always have bands allocated to electric hearing and bands allocated to nonelectric hearing, the sum total of these bands constituting the complete spectrum of the prosthesis to which the prescription is directed, and none of these bands overlapping with respect to the electric hearing and the nonelectric hearing. In this regard, because the methods detailed herein always result in such, these methods further differentiate from a fitting process for a recipient with residual hearing, where bands can overlap and bands can be completely unused by the prostheses (unused by the electric hearing component and on used by the nonelectric hearing component).

In a method as described above and/or below, the method further comprises setting a frequency ceiling of an acoustic hearing aid based on the prescription, and setting a frequency floor of a cochlear implant based on the prescription. In a method as described above and/or below, the data relating to acoustic hearing indicates contributions of consecutive and cumulative frequency bands from high to low frequency for acoustic hearing. In a method as described above and/or below, the method further comprises comparing relative contributions of the respective frequency bands for acoustic hearing of the recipient to relative contributions of corresponding respective frequency bands for electric hearing to determine which frequency bands provide for higher relative contributions for electric hearing and which frequency bands provide for higher relative contributions for acoustic hearing and identifying in the prescription at least one of a frequency band or a frequency based on the determination, the identified at least one of a frequency band or a frequency being indicative of a demarcation between electric hearing and acoustic hearing for the hearing prosthesis. In a method as described above and/or below, the data relating to electric hearing indicates contributions of consecutive and cumulative frequency bands from low to high frequency for electric hearing.

In a method as described above and/or below, the cochlear implant has respective channels for respective sound frequency bands, the comparison indicated that for a first frequency band from the respective sound frequency bands and for frequency bands from the respective sound frequency bands below that first frequency band, cumulative contribution for the second type of hearing stimulation is greater than the cumulative contribution for the electric stimulation, the action of setting the cochlear implant includes at least one of deactivating channels or not activating channels corresponding to frequency bands at and below the first frequency band. In a method as described above and/or below, the data for the second type of hearing stimulation is relative cumulative contribution data for respective frequency bands of descending frequency.

In a method as described above and/or below, the data for non-cochlear implant hearing comprises data developed by progressively eliminating frequency bands from sound exposed to an individual corresponding to the recipient of a multimodal prostheses and determining contributions to speech understanding for the cumulative frequency bands eliminated, wherein the data for non-cochlear implant hearing is obtained after implantation of the cochlear implant into the recipient. In a method as described above and/or below, the data for non-cochlear implant hearing comprises data developed by progressively eliminating frequency bands from sound exposed to a statistically signification group of individuals and determining contributions to speech understanding for the cumulative frequency bands eliminated, wherein the data for non-cochlear implant hearing is obtained prior to implantation of the cochlear implant into the recipient.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, and it is not otherwise noted that such is not the case.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. An apparatus, comprising:
an electrical hearing stimulating device configured to be implanted in a recipient, wherein
the apparatus is set such that the electrical hearing stimulating device evokes a hearing precept in the recipient only in a frequency range that is based on a cumulative contribution for electric stimulation of the hearing system of the recipient, wherein the frequency range is limited such that the apparatus provides superior speech perception to the recipient relative to that which would be the case if the frequency range extended into lower frequencies than the lowest frequency of the frequency range.

2. The apparatus of claim 1, wherein:
the apparatus is a bimodal hearing prosthesis;
the apparatus is configured to provide non-electrical stimulation to the recipient for sound frequencies outside the frequency range but not within the frequency range; and
the apparatus is configured such that the non-electrical stimulation for the sound frequencies outside the frequency range results in superior speech perception to the recipient relative to that which would be the case if non-electrical stimulation by the apparatus was extended into the frequency range.

3. The apparatus of claim 1, wherein:
the apparatus is a bimodal hearing prosthesis;
the apparatus is configured to at least reduce an amplitude of sound waves of ambient origin reaching a middle ear of the recipient; and
the apparatus is configured to provide non-electrical stimulation for sound frequencies corresponding to frequencies below the frequency range.

4. The apparatus of claim 1, wherein:
the apparatus is unimodal hearing prosthesis.

5. The apparatus of claim 1, wherein:
the electrical stimulating device is not fitted to the recipient.

6. The apparatus of claim 5, wherein:
the electrical stimulating device is a cochlear implant including a conventional electrode array extending into a basal region of the cochlea.

7. The apparatus of claim 6, wherein:
the conventional electrode array extends into an apical region of the cochlea.

8. The apparatus of claim 1, wherein:
the electrical stimulating device is fitted to the recipient.

9. The apparatus of claim 1, wherein:
the apparatus is a bimodal hearing prosthesis;
the apparatus is configured to provide non-electrical stimulation to the recipient for sound frequencies outside the frequency range; and
the apparatus is set such that non-electrical stimulation and electrical stimulation are applied only within respective frequency boundaries that result in maximization of information reception by the recipient relative to that which would be the case for other boundaries even with increased amplification of the non-electrical stimulation.

10. The apparatus of claim 1, wherein:
the apparatus is attached to the recipient, and an electrode array is implanted in a cochlea of the recipient; and
the recipient has normal hearing at the lowest frequency of the frequency range.

11. The apparatus of claim 1, wherein:
the apparatus is attached to the recipient, and an electrode array is implanted in a cochlea of the recipient; and
the recipient has no acoustic hearing aid.

12. The apparatus of claim 1, wherein:
the electrical hearing stimulating device is implanted in a recipient.

13. The apparatus of claim 12, wherein:
the recipient is a human.

14. A method, comprising:
setting a cochlear implant to operate based on data based on a comparison of first data for electric stimulation to evoke a hearing percept with second data for a second type of stimulation to evoke a hearing percept different from the electric stimulation, wherein
at least one of:
the first data is data based on a cumulative contribution for electric stimulation; or
the second data is data based on a cumulative contribution for the second type of hearing stimulation.

15. The method of claim 14, wherein:
the first data is data based on the cumulative contribution for electric stimulation; and
the second data is data based on the cumulative contribution for the second type of hearing stimulation;
the cochlear implant has respective channels for respective sound frequency bands;
the comparison indicated that for a first frequency band from the respective sound frequency bands and for frequency bands from the respective sound frequency bands below that first frequency band, cumulative contribution for the second type of hearing stimulation is greater than the cumulative contribution for the electric stimulation; and the action of setting the cochlear implant includes at least one of deactivating channels or not activating channels corresponding to frequency bands at and below the first frequency band.

16. The method of claim 14, wherein:

the data for the second type of hearing stimulation is relative cumulative contribution data for respective frequency bands of descending frequency.

17. The method of claim 14, further comprising:

operating the prosthesis based on the setting so that the prosthesis evokes a hearing percept in a recipient of the prosthesis based on the setting, wherein the prosthesis is not fitted to the recipient when the hearing percept is evoked.

18. The method of claim 14, wherein:

the setting of the cochlear implant results in the cochlear implant not providing stimulation below a given frequency, wherein the comparison indicates that for frequencies below the given frequency the second type of stimulation provides more information to the recipient than that which results from electric stimulation without acoustic stimulation and/or without amplified acoustic stimulation, and for frequencies at and above the given frequency, electric stimulation provides more information than that which results from the second type of stimulation without electric stimulation.

19. The method of claim 14, wherein:

the action of setting the cochlear implant maximizes the second type of stimulation at frequency bands where the electric stimulation provides inferior speech perception relative to the second type of stimulation, and maximizes the second type of stimulation at no other frequency bands.

20. The method of claim 14, wherein:

the first data includes data relating to at least one frequency that evoked both a hearing percept using the second type of stimulation and an electric hearing percept in the recipient of the cochlear implant.

21. The method of claim 14, wherein:

the first data is data based on only band contributions for electric stimulation.

22. The method of claim 14, wherein:

the cochlear implant has respective channels for respective sound frequency bands;

the comparison indicated that for a first frequency band from the respective sound frequency bands and for frequency bands from the respective sound frequency bands below that first frequency band, the cumulative contribution for the second type of hearing stimulation is greater than the cumulative contribution for the electric stimulation.

23. The method of claim 14, wherein:

the first data is data based on results of first hearing test(s) for electrical stimulation; and the second data is data based on results of second hearing test(s) different from the first hearing test(s), the second hearing test(s) for the second type of stimulation.

24. The method of claim 14, wherein:

the setting of the cochlear implant results in the cochlear implant not providing electrical stimulation below a given frequency, wherein the comparison indicates that for frequencies below the given frequency the second type of stimulation provides more information to the recipient than that which results from electric stimulation without acoustic stimulation and/or without amplified acoustic stimulation, and for frequencies at and above the given frequency, electric stimulation provides more information than that which results from the second type of stimulation without electric stimulation.

25. A method, comprising:

obtaining data relating to electric hearing;

obtaining data relating to acoustic hearing;

preparing a prescription for a hearing prosthesis for an individual based on the obtained data relating to the electric hearing and the acoustic hearing;

setting a frequency ceiling for the acoustic hearing based on the prescription; and setting a frequency floor for the electric hearing based on the prescription.

26. The method of claim 25, further comprising:

setting the frequency floor of a cochlear implant based on the prescription.

27. The method of claim 25, wherein:

the data relating to acoustic hearing indicates contributions of consecutive and cumulative frequency bands from higher to lower frequency for acoustic hearing.

28. The method of claim 25, further comprising:

providing an acoustic hearing test to the recipient of the prescription to obtain the data relating to acoustic hearing, the action of providing the acoustic hearing test including:

progressively blocking frequencies falling within frequency bands in a descending manner with the previously blocked frequency bands remaining blocked, thereby obtaining relative contributions of the respective frequency bands for acoustic hearing of the recipient;

comparing relative contributions of the respective frequency bands for acoustic hearing of the recipient to relative contributions of corresponding respective frequency bands for electric hearing to determine which frequency bands provide for higher relative contributions for electric hearing and which frequency bands provide for higher relative contributions for acoustic hearing; and identifying in the prescription at least one of a frequency band or a frequency based on the determination, the identified at least one of a frequency band or a frequency being indicative of a demarcation between electric hearing and acoustic hearing for the hearing prosthesis.

29. The method of claim 25, wherein:

the data relating to electric hearing indicates contributions of consecutive and cumulative frequency bands from lower to higher frequency for electric hearing.

30. The method of claim 25, wherein:

the prescription is for an individual who has received or will receive the hearing prosthesis; and the method further comprises:

obtaining access to the hearing prosthesis; and setting the hearing prosthesis to operate in accordance with the obtained prescription.

31. The method of claim 25, wherein:

the prescription is for a person who has received or will receive a cochlear implant and the prescription prescribes no amplification for at least some frequencies outside of a frequency range prescribed for the cochlear implant.

32. The method of claim 25, further comprising:
after the prescription is prepared, based on the obtained prescription, applying inputs to a processor of a hearing prosthesis system, the hearing prosthesis system being a multimodal system having an acoustic mode and an electrical mode, to generate stimuli for the acoustic mode and to generate stimuli for the electrical mode; and
altering the acoustic mode and the electrical mode of the hearing prosthesis system based on results of the applied input.

33. The method of claim 25, further comprising:
fitting the hearing prosthesis based on the prescription for a hearing prosthesis.

34. A method, comprising:
obtaining data relating to a first type of stimulation;
obtaining data relating a second type of stimulation different from the first type of stimulation;
preparing a prescription for a hearing device for an individual based on the obtained data relating to the first type of stimulation and the second type of stimulation;
providing a hearing test to the recipient of the prescription to obtain the data relating to the first type of stimulation, the action of providing the hearing test including:
progressively blocking frequencies falling within frequency bands in a descending manner with the previously blocked frequency bands remaining blocked, thereby obtaining relative contributions of the respective frequency bands for hearing evoked based on the first type of stimulation of the recipient;
comparing relative contributions of the respective frequency bands for hearing evoked based on the first type of stimulation of the recipient to relative contributions of corresponding respective frequency bands for hearing evoked based on the second type of stimulation to determine which frequency bands provide for higher relative contributions for hearing evoked based on the second type of stimulation and which frequency bands provide for higher relative contributions for hearing evoked based on the first type of stimulation; and
identifying in the prescription at least one of a frequency band or a frequency based on the determination, the identified at least one of a frequency band or a frequency being indicative of a demarcation between hearing evoked based on the first type of stimulation and hearing evoked based on the first type of stimulation for the hearing device.

* * * * *